United States Patent [19]

Levy et al.

[11] Patent Number: 5,339,256
[45] Date of Patent: Aug. 16, 1994

[54] EXPERT SYSTEM FOR ANALYZING EDDY CURRENT MEASUREMENTS

[75] Inventors: Arthur J. Levy, Schenectady; Jane E. Oppenlander, Scotia; David M. Brudnoy, Albany; James M. Englund; Kent C. Loomis, both of Clifton Park, all of N.Y.

[73] Assignee: The United States of Americas as represented by the United States Department of Energy, Washington, D.C.

[21] Appl. No.: 797,622

[22] Filed: Nov. 27, 1991

[51] Int. Cl.⁵ .............................................. G06F 15/46
[52] U.S. Cl. ...................................... 364/506; 364/507; 364/552; 395/911
[58] Field of Search ............... 364/506, 507, 552, 556; 395/911, 914; 324/225, 226, 228, 216, 238, 237

[56] References Cited

U.S. PATENT DOCUMENTS

| | | | |
|---|---|---|---|
| 4,213,183 | 7/1980 | Barron et al. | 364/507 |
| 4,541,064 | 9/1985 | Livingston | 364/552 |
| 4,751,461 | 6/1988 | McWhirter et al. | 364/507 X |
| 4,763,274 | 8/1988 | Junker et al. | 364/481 |
| 4,896,278 | 1/1990 | Grove | 364/552 |
| 4,959,964 | 9/1990 | Singh | 364/507 X |
| 4,979,124 | 12/1990 | Sachse et al. | 364/507 |
| 5,043,663 | 8/1991 | Lam | 364/507 X |
| 5,144,565 | 9/1992 | Brown et al. | 364/507 |

Primary Examiner—Kevin J. Teska
Attorney, Agent, or Firm—Virginia B. Caress; William R. Moser; Richard E. Constant

[57] ABSTRACT

A method and apparatus (called DODGER) analyzes eddy current data for heat exchanger tubes or any other metallic object. DODGER uses an expert system to analyze eddy current data by reasoning with uncertainty and pattern recognition. The expert system permits DODGER to analyze eddy current data intelligently, and obviate operator uncertainty by analyzing the data in a uniform and consistent manner.

18 Claims, 20 Drawing Sheets

Microfiche Appendix Included
(11 Microfiche, 1000 Pages)

EXPERT SYSTEM FOR ANALYZING EDDY CURRENT MEASUREMENTS

MICROFICHE APPENDIX

The present invention has a microfiche Appendix which contains 11 microfiche and 1000 frames.

BACKGROUND OF THE INVENTION

1. Field of the Invention

This invention relates generally to non-destructive testing of metallic material. More particularly, it relates to analyzing eddy current tests.

The Government has rights in this invention pursuant to Contract No. DE-AC12-76-SN00052 between the U.S. Department of Energy and the General Electric Company.

2. Description of Related Art

In this technology, an eddy current probe senses any flaws in a metallic object. The eddy current probe may be a dual bobbin probe that has two electromagnetic coils which may be operated separately (in an absolute mode) or together (in a differential mode). As the probe is passed over a flaw in the metallic object, the current (eddy current) within the metallic object changes due to the flaw. These current changes within the metallic object are detected as a change in electrical impedance of the probe's coil. The impedance of the coil is then recorded as an electrical signal on a storage device.

Once these electrical signals are stored on the storage device, the signals must be analyzed by a human operator. The human operator bases his analysis on a set of guidelines which guide the operator's analysis. The difficulty of human analysis of eddy current signals is that the guidelines are interpreted in any number of different ways depending on which operator is doing the analysis. In addition, a single operator may be inconsistent in his analysis. This makes comparisons of two separate analyses almost impossible because of the inconsistent nature of the application of the guidelines. An operator also may inadvertently introduce his own bias and beliefs into the analysis process.

In addition, the guidelines are frequently changed as new analysis techniques are developed. The operator must be constantly retrained as new guidelines are created. Also, an operator's sizing of flaws, based on his own visual analysis, is inconsistent from flaw to flaw and analysis to analysis due to human limitations.

The actual analysis done by a human operator, in addition to being inconsistent, is also time consuming and expensive. Much of the analysis requires doing the same steps over and over again until a diagnosis is reached.

The signals generated by the probe are typically displayed on a CRT screen and form visual patterns which are interpreted by an operator. The interpretation of eddy current data can be quite complex as any phenomena which affects the electrical impedance of the probe coil will generate visible patterns. Combinations of these patterns can make interpretation and sizing of a flaw very difficult.

Other computer based systems have been developed which offer automated interpretations of eddy current data. These systems are available from a variety of vendors. However, none of the previous systems emulate a human operator's interpreting process including reasoning with uncertainty and pattern recognition. A substantial body of knowledge is then applied during this interpretation process requiring many factors to be considered. Prior systems that achieve these goals use human operators as the primary interpreters. These generally fail to use all of the pertinent information or impose some bias that makes later comparison subjective.

SUMMARY OF THE INVENTION

It is therefore an object of the present invention to provide an expert system which will analyze eddy current test data from metallic objects, especially for heat exchanger tubes.

It is another object to provide an eddy current data analysis system which can emulate a human analyst who reasons about observed data patterns, but can do so with uniform interpretation results.

It is another object of the present invention to provide an expert system which can automatically calibrate itself.

It is another object of the present invention to provide an expert system which can easily assimilate new knowledge.

It is another object of the present invention to provide an expert system for analysis of eddy current data which can reason with uncertainty and recognize patterns of two dimensional point-ordered figures.

It is another object of the present invention to provide an expert system for eddy current data analysis which includes an open operator statement window which allows an operator to assert his opinions in plain English which will then be taken into account by the expert system.

The invention is a diagnostic system that interprets eddy current signals. The framework of the diagnostic system is an expert system called DODGER. The process of interpreting eddy current signals to diagnose the probable damage mechanism, or flaw, requires the examination of many complex signals and their mutual interaction. The key advantage of the expert system approach is a rapid and uniform application of interpretation guidelines. Additionally, changes or additions in interpretation guidelines are easily accommodated without changing the basic structure of the system.

The DODGER system includes a reasoning with uncertainty capability for dealing with inconsistent or contradictory data and facts and an automatic pattern recognition capability for deriving key parameters from the graphical data in an objective manner.

BRIEF DESCRIPTION OF THE DRAWINGS

These and other objects, features and advantages of this invention will become more clear from the following detailed description of the preferred embodiment when considered in connection with the accompanying drawings, wherein like parts in each of the several figures are identified by the same reference numbers, and wherein:

FIG. 3 shows the diagnosis of a flaw by the DODGER system;

FIG. 16 shows evaluation of prime frequency data by DODGER;

DETAILED DESCRIPTION OF THE PREFERRED EMBODIMENT

Various aspects of the preferred embodiment of the eddy current analysis system, known as "DODGER" will now be described in detail with reference to the drawings.

Architecture of DODGER

Figure 1:
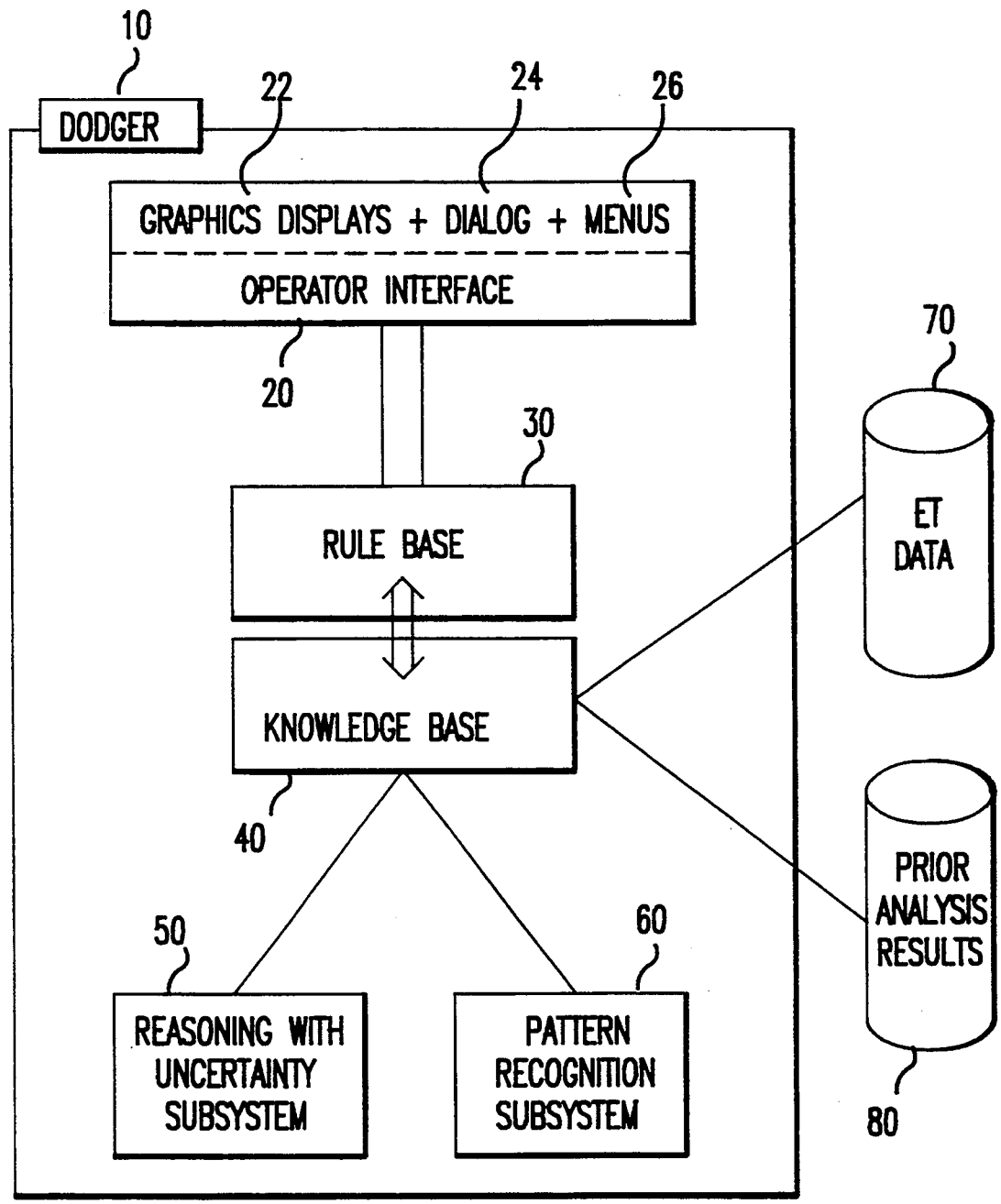
FIG. 1 shows the architecture of the DODGER expert system.

The architecture of DODGER will be described in terms of five major functional components, namely the Operator Interface, the Rule Base, the Knowledge Base, the Reasoning With Uncertainty Subsystem, and the Pattern Recognition Subsystem. These components are highly integrated in the implementation of DODGER due to its nonprocedural nature. FIG. 1 shows the conceptual structure and interrelationship of these components.

The Operator Interface 20 which allows interaction between DODGER and an operator, partitions the system graphical display into three distinct regions. The first region is an interactive graphical display 22 which presents various graphical representations of eddy current signal being analyzed. A second area of the screen is a menu system 26 which allows an operator to select configuration options and operational commands in order to perform the analysis. Finally, a third area of the screen is a dialogue area 24 (called the command window) which allows the operator to provide information requested by DODGER and to enter opinions that may influence DODGER's reasoning process.

The heart of the system is its knowledge base 40. It is the repository of all facts used by DODGER to guide its line of reasoning. These facts include static knowledge about heat exchangers and damage mechanisms as well as dynamic facts asserted by the reasoning with uncertainty system, the pattern recognition subsystem and the operator.

The rule base 30 encodes the reasoning strategies available to DODGER and controls the overall operation of the system. The rules rely heavily on facts in the knowledge base to select and follow a suitable line of reasoning.

The reasoning with uncertainty subsystem 50 operates on physical measurements recorded in the knowledge base to arrive at a belief value for each of the known damage mechanisms. These values enable rules to pursue the most promising line of reasoning based on the knowledge available at the time.

The pattern recognition subsystem 60 analyzes figures known in the art as Lissajous figures and asserts facts about geometric characteristics of those figures and stores those facts as geometrical parameters (physical measurements). DODGER uses these facts to identify and characterize the mechanisms that are responsible for a selected indication.

Each of these components is described in more detail in the following sections.

Operator Interface

DODGER's operator interface allows an operator to examine data and analyze indications in a flexible manner by presenting information in a way that is very natural in the domain of eddy current data analysis. The graphical display provides two different modes for graphical evaluation of the data. The specific use of the two graphical modes will be described below in the section titled "Operation of the DODGER System". These two modes are required since the eddy current signals are two-dimensional (having both a horizontal and a vertical component) and the signals vary with time.

Figure 2A:
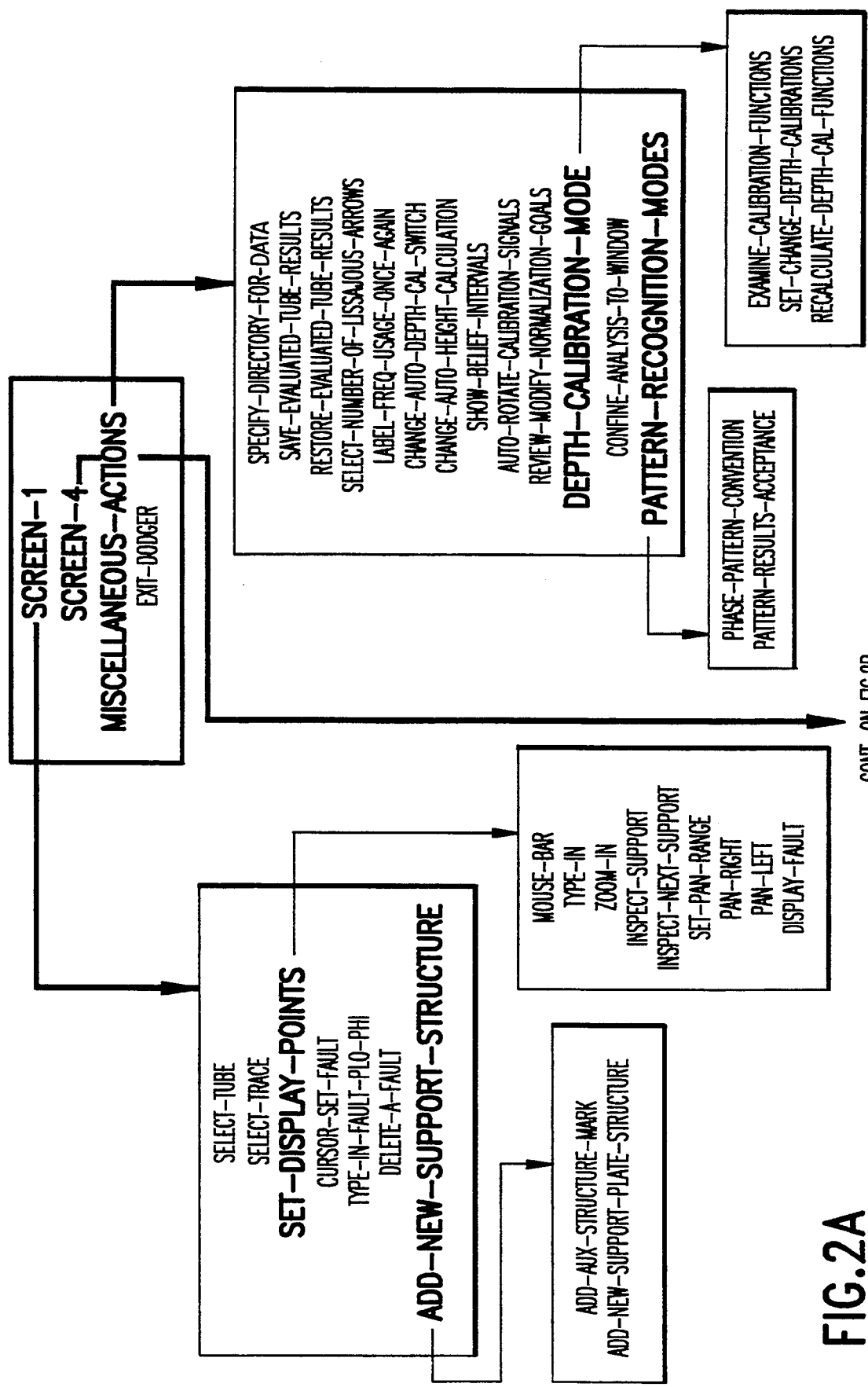
FIGS. 2A and 2B show DODGER's menu system.
Figure 2B:
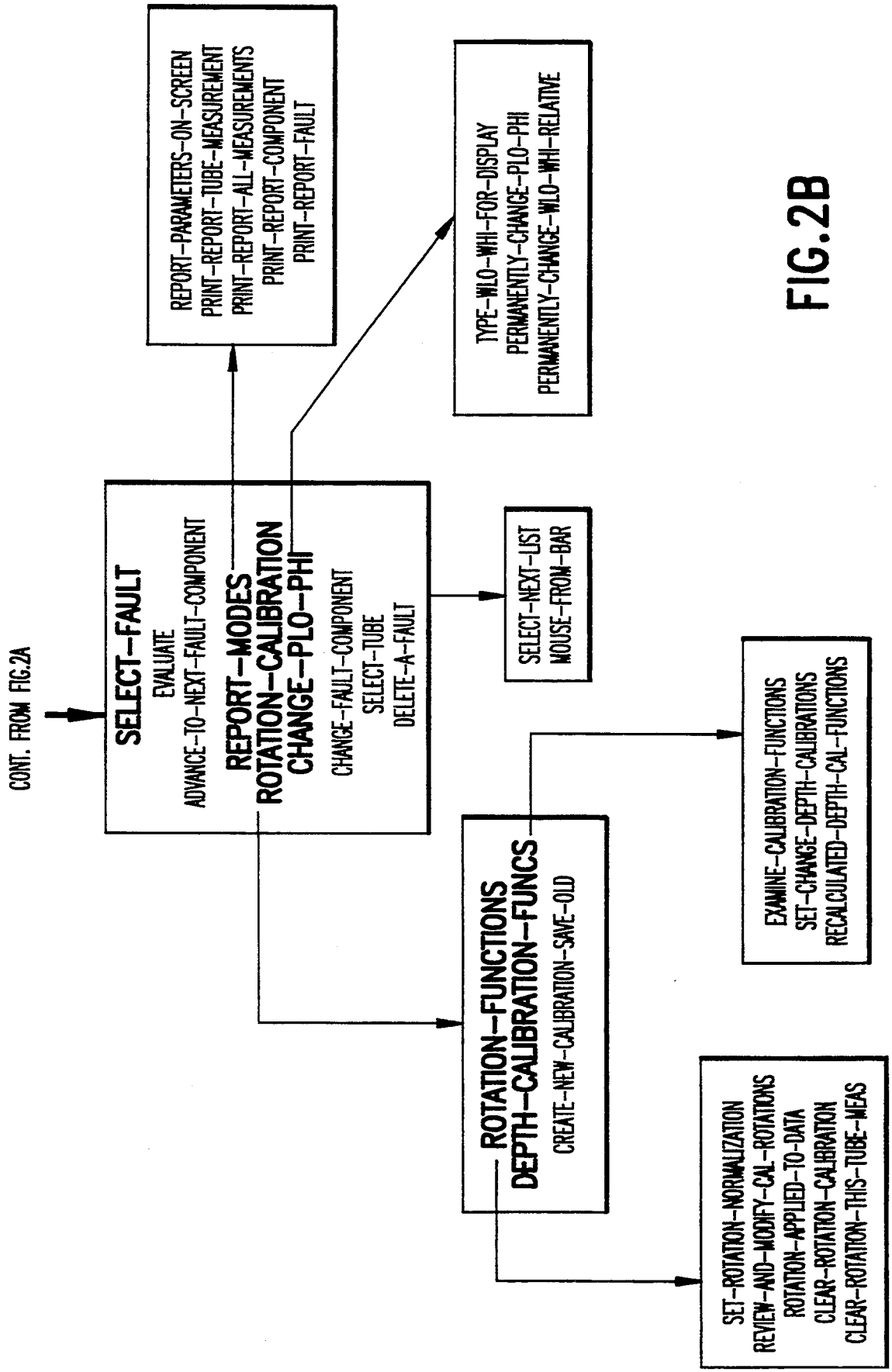

In order to select data to be analyzed, the operator chooses options from the menu display. DODGER presents a menu of available heat exchanger tubes and displays data for the ones selected by the operator. The menu system is also used to switch between the two screen modes, as described above, and to specify operational commands instructing DODGER what to do next (e.g., select a flaw, or display a different frequency signal). FIG. 2 shows the selections available from the menus.

An operator may enter instructions through the dialogue window. All operations which do not require information from the operator are performed automatically. When DODGER requires additional information to complete an evaluation, the information is solicited from the operator through the dialogue window. Similarly, DODGER queries the operator to confirm a diagnosis and to examine suspicious cases. In addition, the operator is free to assert his own opinions at any time during the evaluation by using the dialogue window. DODGER will take any such suggestions into account in its reasoning process.

Rule Base

The rules employed in DODGER are specialized to the interpretation of eddy current data patterns. Specifically, they allow DODGER to determine a strategy for producing a diagnosis of the probable mechanisms for a given indication, how extensive the indication is, and its relations to other known indications. In addition, the rules in DODGER manage the complex procedures required to perform intelligent interpretations of the data such as calibrations and signal mixing.

Central to the effectiveness of the rules is the problem of determining when individual rules should act (or be "activated"). Each rule specifies a set of facts that must exist in order for the rule to be activated. The result of rule activation is often the assertion of new facts or deductions, which in turn may satisfy the fact requirements of other rules. Thus, lines of deduction are chained by a succession of rule activations.

One novel aspect of DODGER is that the expertise of several skilled individuals, well versed in the technical operation of interpreting indications from eddy current signals, has been encoded into a collection of rules. No other system exists wherein a number of skilled eddy current analysis individuals shall have had their knowledge used simultaneously for analysis.

These rules fall into the following categories:

1. Control rules. These affect the order in which operations are performed, such as those that describe a systematic approach to calibration.
2. Constraint rules. These define the boundary limits of what is reasonable given existing situations.
3. Diagnostic rules. These formulate a dynamic strategy for deciding which is the most likely line of reasoning to follow.
4. Sludge rules. These contain specific knowledge on how sludge formations on heat exchanger tubes can be deduced from available facts.
5. Multiple Component rules. These represent those cases where a single fault indication is attributable to more than one damage mechanism.
6. Pattern Recognition rules. These evaluate the consequences of facts asserted by the pattern recognition analysis subpart.

Each of these classes of rules is described in more detail in the following paragraphs.

1. Control Rules

Although DODGER is designed to operate non-procedurally, there are cases where it is necessary to control the order in which some information is processed. This is the case when there is no actual dependency in the data itself. It is necessary to implement control rules in order to force a certain order on the operation of DODGER. For example, control rules manage the menu system.

A novel function of the control rules is the automatic and "intelligent" calibration of the measurement system. This involves a complex sequence of operations including signal rotations, normalizations and the creation of specially derived signals known as "mixed" signals. The actual sequence of operation depends on the current state of the data. DODGER strives to calibrate the data with the fewest possible operator interactions. In this respect, DODGER's operation is much faster and more reliable than previous methods.

In addition, flaw depth versus phase functions are derived, as well as other signal attributes. This all occurs without the operator specifying any commands; merely responding to a few specific questions as DODGER requests information that it cannot deduce itself.

The control rules include a sparse natural language interface that enables the operator to comment and direct DODGER to consider or reconsider various hypotheses. The natural language interaction allows the operator to comment on DODGER's interpretation at any time. A statement may express direction, such as "try looking for sludge", or a statement may express disbelief, such as "I don't believe that corrosion is involved in this indication." If the operator's comment is used in enhancing the diagnosis, it becomes a permanent part of the diagnosis record.

2. Constraint Rules

The purpose of constraint rules is to anticipate certain well defined conditions in an evaluation of an indication and respond to the circumstances in a uniform manner. The response of some of these rules is to redistribute assigned belief for a particular set of circumstances. Others may ask the operator to comment on an ambiguous situation or contradiction.

The intention of grouping the rules in this manner is that as additional knowledge is acquired about the data environment, that knowledge can be easily added as additional constraints in the diagnosis process. Many of these rules insert a fact in the knowledge base that identifies the nature of the constraint so that a diagnosis trace can be made after the fact. These constraint facts are included in the diagnosis report.

3. Diagnostic Rules

The diagnostic rules are concerned with two things: gathering information as expeditiously as possible, and deciding what hypotheses are the most believable from the available knowledge.

In order to make the best decisions, an initial strategy is developed and is then updated as each new fact is obtained. In this manner, DODGER does not solicit information that is not needed in pursuing a hypothesis. Only in cases where the outcome is confused by contradictory or misleading facts does DODGER solicit additional pieces of information.

The initial strategy that is formed lays out a plan for each specific hypothesis and specifies which frequency signals are best to examine in order to confirm or disconfirm the hypothesis. As the hypothesis is pursued, the strategy is shifted to accommodate any new deduction paths. Often, several hypotheses will be pursued simultaneously. These hypotheses may be initiated by different components of DODGER.

The diagnostic rule set is guided by a number of constraints that conform to common sense practice. For instance, even if the first observation suggests maximum belief in some outcome, it is not desirable to base a decision on only one piece of evidence. Further evidence is sought to confirm or to disconfirm the indication.

4. Sludge Rules

Sludge is among the most complex of hypotheses, specifically relevant to heat exchanger applications, that is diagnosed in DODGER. Sludge differs from the rest of the damage mechanisms since it frequently occurs in domains that encompass several adjacent fault areas in neighboring tubes. It is often possible to deduce information about the macroscopic structure of sludge domains by properties of the entire set of facts. DODGER is capable of recognizing sludge domains in clusters of heat exchanger tubes. The macroscopic sludge mapping aids in the diagnosis of sludge formation.

DODGER is also capable of detecting a sludge indication that is related to a physical deposit on an adjacent tube, where the signal is sensed over the gap between tubes. The non-procedural nature of DODGER enables it to maintain an awareness of potential cases of this sort long after the tube has been evaluated. If an adjacent tube exhibits specific characteristics upon subsequent tube evaluation, DODGER will return to the former tube and update the diagnosis. No other system has this capability.

5. Multiple Component Rules

Every hypothetical fault is presumed to have one or more components. This implies that more than one mechanism may be acting simultaneously to produce an indication. For instance, a corrosion spot may also be at the site of a dent. In this situation, it may be desirable to hypothesize that one of the faults is causally related to the others. DODGER does just that in the case where more than one hypothesis appears to be supported by the signals.

The multiple component rules reason through these complex indications and attempt to resolve them into multiple components that may be interrelated.

6. Pattern Recognition Rules

The pattern recognition subsystem examines Lissajous figures as they are displayed on the screen. Certain classes of well formed patterns are recognized and characterized. These patterns that are recognized by DODGER comprise two main classes: "FIG.-8" curves and "FIG.-V" curves. These two general classes include many significant cases of material defect features.

For these two classes, facts are asserted about the pattern characteristics which include size, orientation, shape and distortion factors. The rules determine if the parameters are reasonable to use in the ensuing diagnosis. DODGER may use one of several different conventions to quantify the pattern. For example, although by default DODGER characterizes a FIG.-8 pattern based on the "linear transition", as it is known in the art, DODGER can alternatively characterize it using peak-to-peak values. In fact, if the operator appears to use an alternate convention DODGER will "notice" it and ask if the convention should be the default.

DODGER allows the operator to select the mode that governs the use of pattern recognition results. In semiautomatic mode, the pattern results are displayed on the Lissajous figure. In this case, the operator can press a button to accept the pattern results or override the pattern results by providing his own measurement. In automatic mode, DODGER's rules will decide if the pattern recognition results are acceptable and the operator is not queried. The modes are selected by an option in the menu system.

While the pattern recognition subsystem does not recognize all Lissajous patterns from real data, those that are recognized are characterized uniformly and accurately. DODGER maintains an awareness of what can be interpreted and what requires human intervention. The combination of algorithmic pattern classification, non-procedural rules of interpretation, and minimal human intervention for difficult cases makes DODGER a very rapid, reliable, and novel evaluation system.

Complete documentation of the rules used in DODGER is found in Appendix I which contains a microfiche computer code listing of the DODGER system.

Knowledge Base

DODGER's knowledge base maintains all of the information (facts) used in the diagnosis. Two types of information reside in a knowledge base, static and dynamic information. The static knowledge applies to all pertinent system components and all measurements DODGER may encounter. Dynamic knowledge consists of the facts relevant to the current structures being analyzed. These are the facts asserted by the various components of DODGER as diagnosis progresses.

The static knowledge DODGER maintains includes established guidelines for interpreting eddy current data as well as individual techniques described by a number of expert human interpreters. This allows DODGER's rules to emulate a human expert, well versed in the interpretation guidelines, and experienced with proven interpretation techniques.

DODGER represents the measurement and the environment of a heat exchanger test as a collection of objects. Certain objects relate to the state of the evaluation while others represent the measurement and its configuration. Many of the objects are specified by a schema. These objects are related to each other by operators. An example of a commonly used operator in DODGER is the inheritance of attributes along certain predefined lines. The rules in DODGER are sensitive to the values associated with attributes of the objects. The rules may modify or add attributes in the schemata. This schema representation of data is a basis for the expert system. Below is an example of the schema used for a heat exchanger representation.

```
(defschema HX
(HX-ref-symbol)          specific HX being inspected BM
(HX-geometry-number)     geometry specifier
(inspection-year)        ID for inspectn yr: # for 'current 1989
(design)                 'horizontal' or 'vertical'
(support)                'complete' or 'partial'
(num-supports)           e.g., 3 (physical)
(dist-btwn-support)      *1
(num-tubes)              total number of tubes
(material)               tube mater'l [select from list]
(resistivity)            [micro-ohm-centimeter]
(wall-thickness)         [inches]
(optimal-freq)           primary frequency for 4.1 standard
(age)                    age of HX [years]
(last-cleaned)           years since cleaned, or nil
(prior inspection))      year of prior inspections
```

*1 (dist-btwn-support (s1 s2 inch)) is the distance between supports s1 -and- s2 in inches. E.g., (DIST-BTWN-SUPPORT HX [1 2 23.5]); between 1 & 2 (DIST-BTWN-SUPPORT HX [0 1 26.25]); between tube-sht & 1

This manner of representing knowledge is not only well suited to heat exchanger measurements, but also to a great number of other measurement problems. It is suitable for any complex system composed of elements that can be hierarchically described.

With all of the schema, objects of lower order schema inherit attributes from higher ordered schema. A hierarchy of schema is created which defines each schema. For example, for a schema for a heat exchange tube, the following hierarchy of schema exists:

TUBE MEASUREMENTS have TUBE-FAULTS
TUBE FAULTS have COMPONENTS
COMPONENTS have DAMAGE hypotheses
DAMAGE (when=sludge) has SLUDGE-STRUCTURE The capitalized words are schema which are related hierarchically as shown.

Faults in a tube are also described using a schema. Thus, the system is able to redefine faults as required by the analysis. Each fault has an attribute which indicates to DODGER whether the fault is a suspected fault (not confirmed) or an already processed fault (known fault). Each fault is modeled as a group of fault components so that multiple causally related faults may be analyzed simultaneously.

Reasoning With Uncertainty Subsystem

Figure 19:
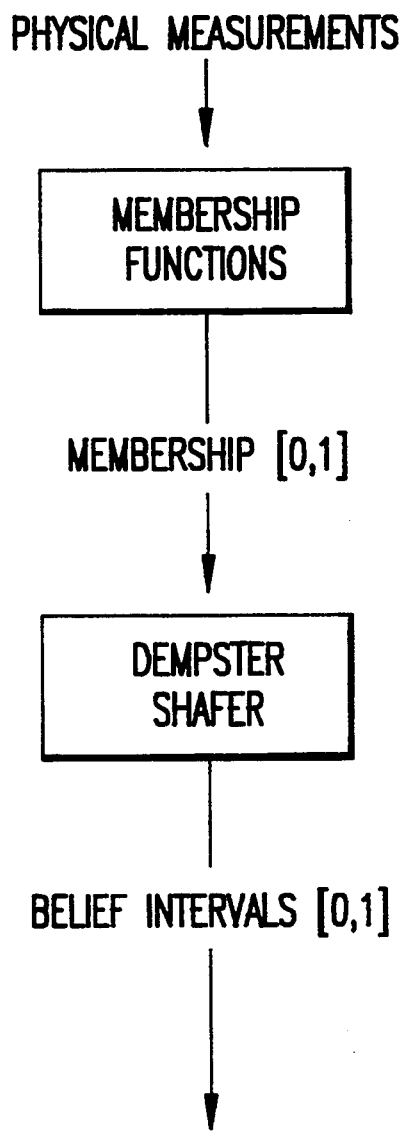
FIG. 19 shows DODGER's reasoning with uncertainty subsystem steps.

FIG. 19 summarizes the steps used in the reasoning with uncertainty subsystem. The objective of the reasoning with uncertainty subsystem is to transform physical measurements of the data pattern such as phase angle and amplitude into belief statements (belief intervals) for each of the possible damage diagnoses.

Analyzing eddy current signals requires the simultaneous consideration of parameters that have dissimilar units of measurement and different value in diagnosis. For example, phase angle, an important measurement parameter is measured in degrees, and amplitude, another measurement parameter is measured in volts. The method used in DODGER to transform evidence from measurements with different units of measure into a single scale that can be combined is an implementation of fuzzy set theory. The fuzzy set representation is also well equipped to represent inexact or incomplete data as is often found in eddy current analysis. For example, probe motion and the presence of multiple faults in a particular location contribute to uncertainty in the phase angle and amplitude measurements.

Phase angle and amplitude are transformed into fuzzy set representations through membership functions as shown in FIG. 19. Membership functions are mathematical functions that map a physical measurement onto a scale of [0,1]. The value of the membership function reflects the degree of belief in a particular damage hypothesis. For example, a membership function value of 0.8 for the damage hypothesis "dent" reflects a relatively high degree of belief.

There are three basic types of membership functions used by DODGER. The first type returns a degree of membership in each of the damage hypotheses based on the amplitude measurement of a single frequency. The second type returns a membership based on the phase angle of a single frequency. Finally, there are functions which return memberships based on the simultaneous behavior of phase angle and/or amplitude at several frequencies.

The evidence, when represented as a collection of fuzzy sets, is combined to yield a belief interval in each possible damage hypothesis using the Dempster-Shafer theory of evidence as shown in FIG. 19. Quantifying the uncertainty in the diagnosis, through the use of belief intervals, is a novel feature for eddy current test analysis. Dempster-Shafer allows DODGER to narrow the hypothesis set as evidence is accumulated; this models how an expert reasons. Another important advantage of this method is that belief and disbelief are accumulated independently. This representation allows ignorance (lack of knowledge) and conflict in evidence to be treated separately.

Dempster-Shafer provides an evidence combination rule which is independent of the order in which evidence is gathered. It is required that the hypotheses to be combined are mutually exclusive and exhaustive. In DODGER, the combination rule is used to obtain belief intervals for each of the individual fault mechanisms. Belief intervals are of the form [belief, plausibility], where belief gives the total amount of belief in the hypothesis and the plausibility gives an upper bound on the belief. The width of the belief interval is a measure of the uncertainty in the diagnosis. The belief interval for the most likely diagnosis is displayed in DODGER's diagnosis window (see FIGS. 3 and 4). Additionally, the belief interval for all possible hypotheses can be displayed graphically in the second mode of operation as discussed earlier and is shown in FIGS. 3 and 4.

The implementation of the Dempster-Shafer evidence combination method is another novel aspect of the DODGER system. In order to calculate belief intervals, all of the evidence must be accumulated for each diagnostic hypothesis. Confirming and disconfirming evidence for each hypothesis is accumulated separately. DODGER implements a technique to represent hypotheses and membership functions so that evidence can be accumulated independent of the order in which it is received and without knowing explicitly the number of diagnostic hypotheses in the system.

This technique represents each hypothesis and each fuzzy set as an entry in the list. As evidence is processed, this list is referenced and each piece of evidence is then assigned to the appropriate accumulator. This is a very important aspect of the invention as it allows the addition, deletion, reordering, or changing of diagnostic hypothesis without altering the evidence combination code. This decoupling between the combination rules and evidence allows DODGER to be easily modified and maintained.

Pattern Recognition Subsystem

The method of computer recognition of patterns implemented in DODGER is described herein. Patterns recognized by this method are restricted to two dimensional curves formed by connecting a sequentially ordered set of points, $((x_i, y_i), i=1,2,\ldots,N)$. An example of such patterns are Lissajous figures which are obtained from eddy current measurements.

Figure 5:
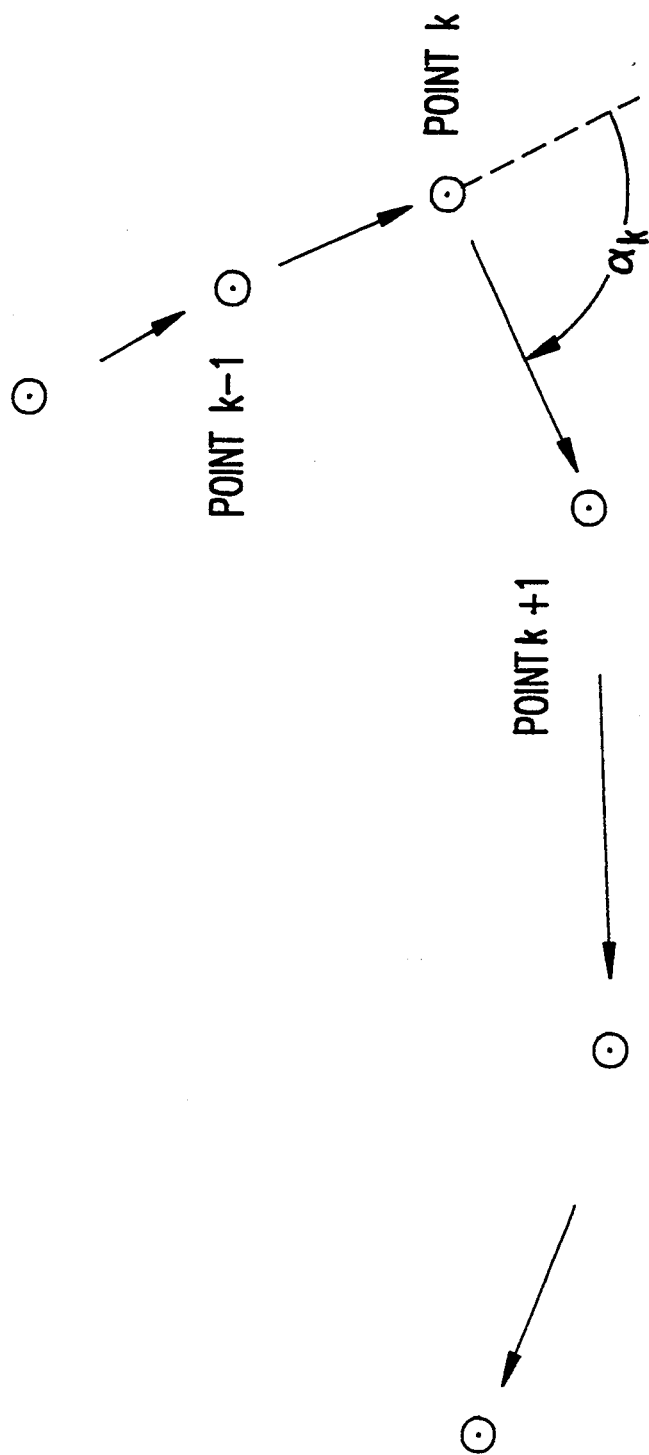
FIG. 5 shows a directed angle which is used to define curvature functions.

Recognition of a pattern means identifying a class to which a given pattern belongs. A pattern class is defined by the sequential "curvature" change along a pattern's arc length. The "curvature" function is given by $$f(S_i) = \sum_{k=1}^{i} a_k \qquad (1)$$

where $a_k$ is the directed angle subtended by the two lines connecting nearest neighbor points to point k, as shown in FIG. 5, and $S_i$ is the arclength from the first point to point i. In between two given points, f(s) is defined by linear interpolation.

An "edge" in f(s) represents a change of curvature in the figure. By convention, the orientation of the curvature change may be either "plus" (counter-clockwise) or "minus" (clockwise). The sequential ordering of significant curvature change defines pattern class, represented symbolically as $(e_1 e_2 \ldots e_m)$, where $e_i$ is either "plus" or "minus", for m significant curvature changes. The determination of $(e_1 \ldots e_m)$ from the set of data points $\{x_i, y_i\}$ is what is meant by pattern recognition in DODGER.

Not all curvature change is "significant". Significant curvature change is a subjective property that depends on the visual resolution of an observer. A machine's visual system, like a human one, must be capable of resolving curvature differences at different levels; those curvature differences above a given level are said to be "significant" and those differences below that level are filtered out.

Filtering of the curvature function is accomplished by utilizing a mathematical operation called "convolution", The filter function, $G_\sigma$, is chosen to be the standard Gaussian function, $$F_f(s;\sigma) = \int_{-\infty}^{\infty} G_\sigma(s-t) f(t) \, dt \qquad (2)$$

$$G_\sigma(u) = \exp(-u^2/2\sigma^2)/\sqrt{2\pi}\,\sigma \qquad (3)$$

Figure 6:
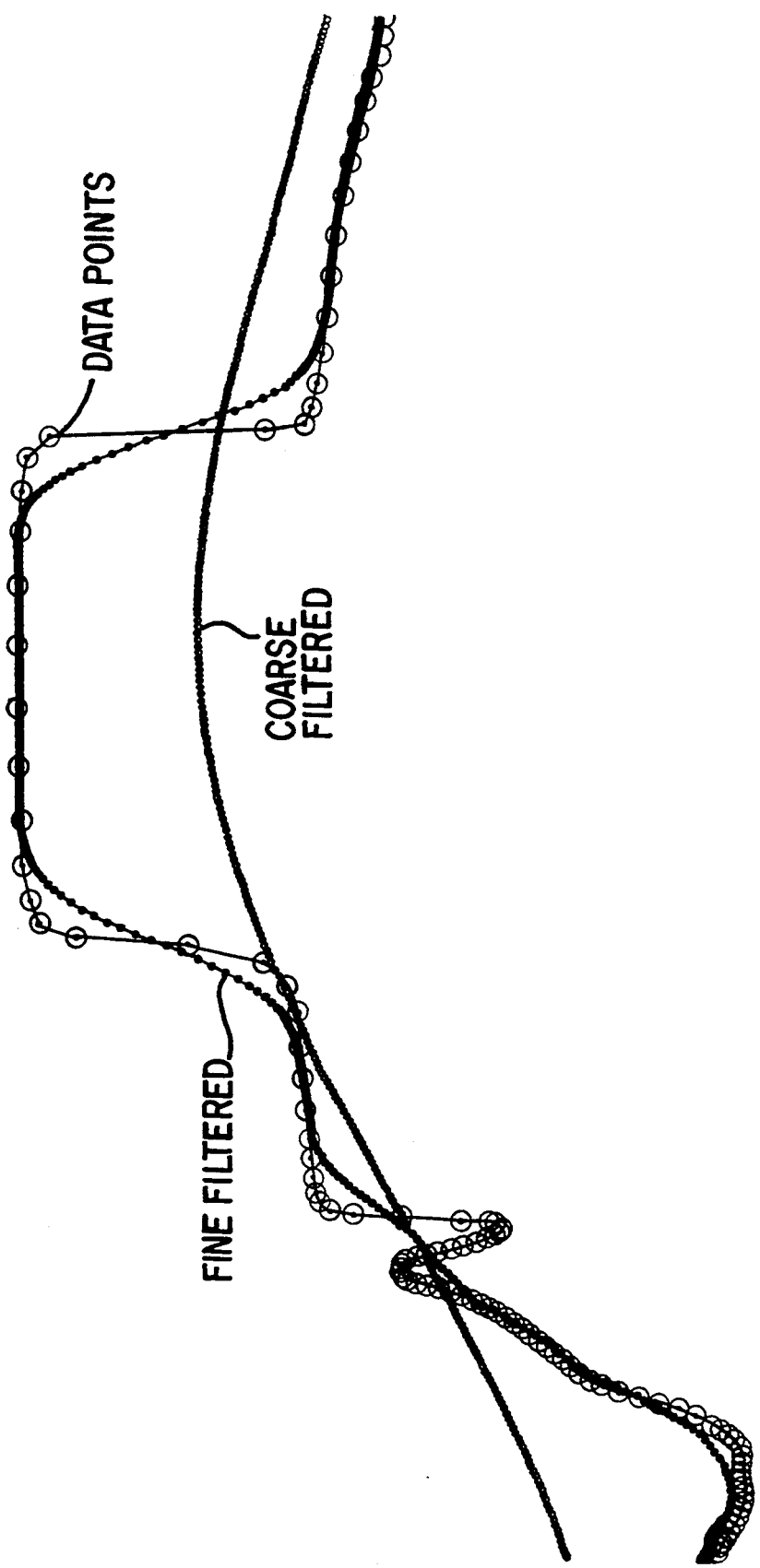
FIG. 6 shows the curvature function and filtered functions.

The parameter $\sigma$ is associated with the resolution, or filtering, level; the larger the value of $\sigma$, the coarser the resolution. FIG. 6 is an example of a curvature function, f, filtered at two resolution levels, coarse and fine.

Figure 7:
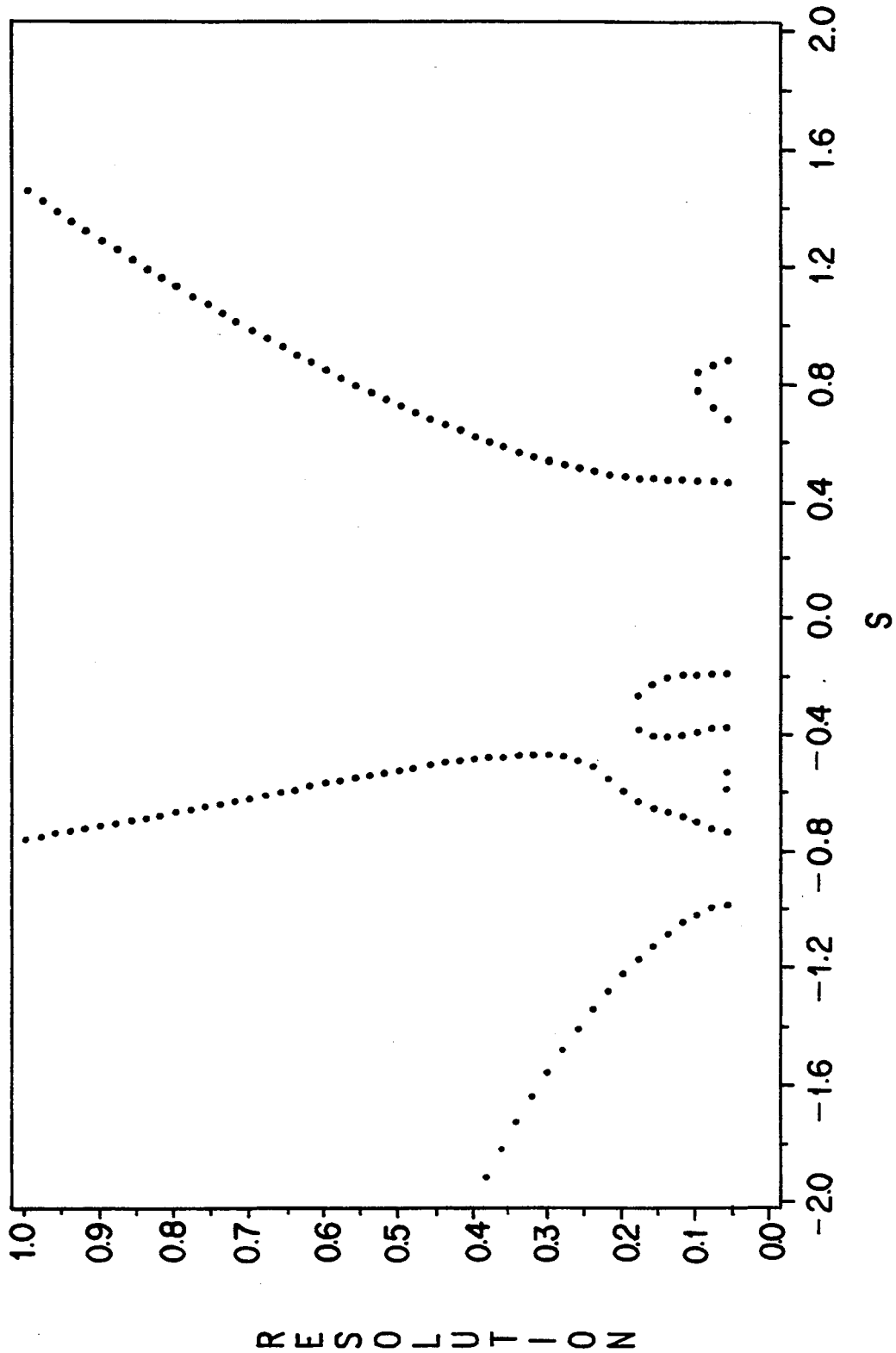
FIG. 7 shows a scalespace representation.

At the location along the pattern's arclength at which curvature change occurs, the first derivative of $F_f$, displays an extremum value; in other words, $$\partial^2 F_f(s;\sigma)/\partial s^2 = 0 \qquad (4)$$

is satisfied. This equation is the fundamental relationship used to recognize a pattern's class and the locations at which the relationship is satisfied are called "zero-crossings". The explicit dependence of $\sigma$ on zero-crossing values is called a "scalespace representation" of the pattern. FIG. 7 is an example of a "scalespace" representation of the curvature function shown in FIG. 6.

In order to properly identify significant curvature edges, zero-crossings are computed at many levels of resolution. This multiscale representation, as it is called, is useful for the following reason. The coarser the resolution of the filtering process, the easier it is to detect the presence of an edge, i.e., the signal-to-noise ratio is better. At the same time, however, the coarser the resolution, the more difficult it is to precisely locate the position of the edge. Conversely, the finer the resolution, the worse is the signal-to-noise ratio, but the localizability of the edge is easier. Using multiscaling, both proper detection and precise location of an edge becomes possible.

The pattern recognition method has the following steps. First, all zero crossings are computed at coarse resolution, thereby identifying potential edges. Second, those scalespace branches corresponding to specific zero crossings are traced as resolution increases so as to properly locate the edges.

Not all zero crossings are associated with "significant" curvature change in the figure. Spurious or "phantom" zero-crossings, not associated with significant curvature change, are also possible, so that further analysis must be performed. At a given level of resolution (fine resolution) all zero-crossings are arranged in increasing order, $Z_1 < Z_2 < Z_3 \ldots < Z_m$, for m different zero-crossings. The midpoints between each pair of zero-crossings are computed and used as boundary points of m intervals, $I_j$, $j = 1, \ldots, m$, thereby partitioning the total pattern arclength. The filtered curvature function $F_f$ restricted to each subinterval, $I_j$ is then reanalyzed.

The scalespace representation of a single edge is always a straight vertical line, i.e., a single zero-crossing at all resolution levels. This should be the scalespace representation within each subinterval, $I_j$, if one zero-crossing, or curvature step, occurs within that subinterval. The height and slope of the step are then computed for the zero-crossing in each subinterval. If the height exceeds that permitted for a given resolution level, then the zero-crossing represents a significant curvature change; otherwise, the zero-crossing is disregarded. Proceeding in this manner for all subintervals, provides the sequence $(e_1 e_2 \ldots e_k)$, $k \leq m$, i.e., the recognition of pattern class.

The partitioning of arclength in the above manner is a very effective and reliable way of identifying significant change in a function. In tests using hundreds of eddy current test patterns, no observed error was detected in computing significant curvature change.

Figure 8A:
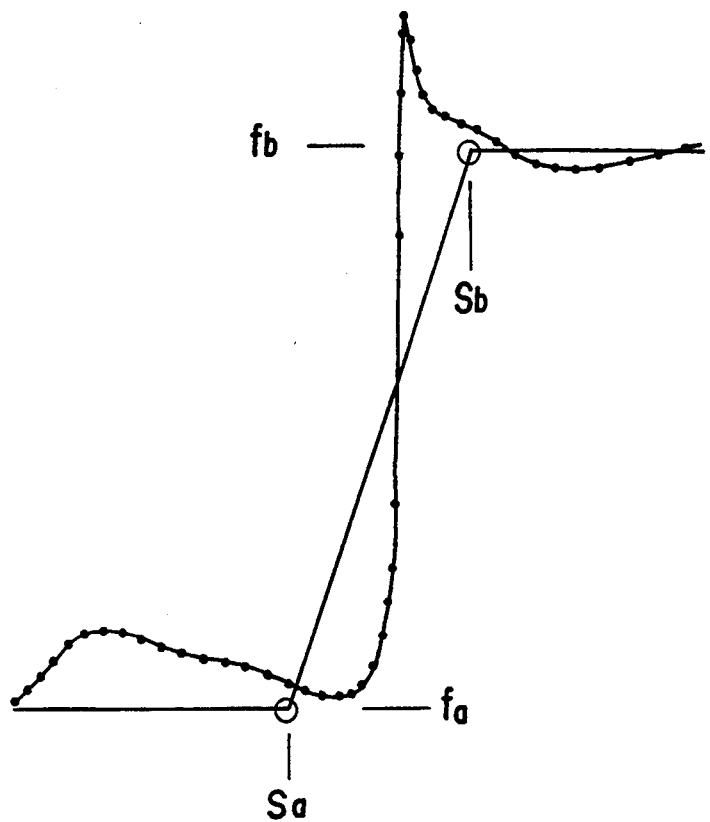
FIGS. 8A and 8B show a single curvature step.
Figure 8B:
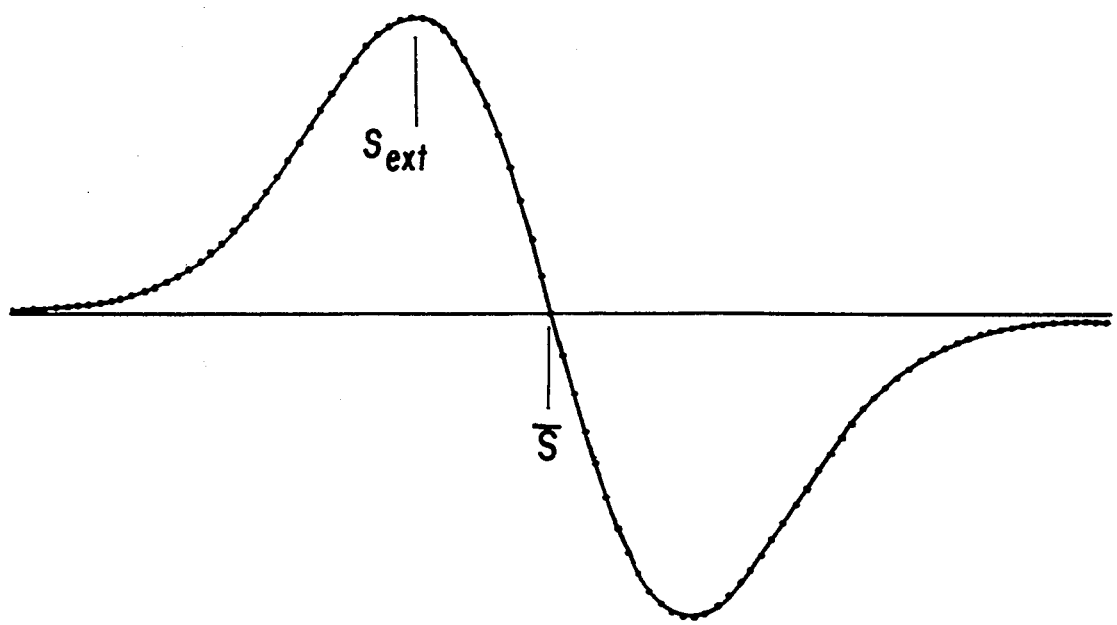

Step-height and step-slope are determined in the following manner. FIG. 8(a) depicts a single filtered curvature edge, also showing the parameters that define an idealized step. FIG. 8(b) shows the function $$F_f''(s;\sigma) \equiv \frac{\partial^2 F_f(s;\sigma)}{\partial s^2} = K[\exp\frac{-(s-s_a)^2}{2\sigma^2} - \exp\frac{-(s-s_b)^2}{2\sigma^2}] \qquad (5)$$

$$= \sum_{i=n1}^{n2} (K_{i+1} - K_i) e^{-(s-s_i)^2/2\sigma^2}$$

Here $K = (f_b - f_a)/(S_b - S_a)$, and $K_i$ is the comparable slope between points i and i+1 in the point set that includes the $n_1$-th through the $n_2$-th points in a partitioned subinterval. At $s = S_{ext}$, $\partial F_f(s;\sigma)/\partial s = 0$, and for large $\sigma$, $$F_f''(S_{ext};\sigma) \approx e^{-0.5} (f_b - f_a)/\sigma, \qquad (6)$$

giving both the orientation and magnitude of the curvature change. The slope K, is determined from $$\frac{-\sigma^2 \, \partial F_f(s;\sigma)/\partial s}{(f_b - f_a)} \bigg|_{s=\bar{s}} = e^{-2\delta/\sigma} \qquad (7)$$

where $\delta = (S_b - S_a)/2$ and $\bar{s}$ is the location of the zero crossing, $\bar{s} = (s_a + s_b)/2$. $s_b$ and $s_a$ can be computed separately from $\delta$ and $\bar{s}$.

Because the procedures described above depend crucially on curvature information, they are very sensitive to "pattern noise" i e large variations of curvature that are unimportant to overall pattern appearance. Three different types of noise have been identified and they are all eliminated from the data set prior to analysis of pattern class. These three noise types are as follows:

1. Random noise—Random noise is defined to be unimportant fluctuations throughout the entire pattern curve. These occur, for example, when a pattern is formed from data accumulated from measurement instruments. This type of noise is removed by an iterative smoothing technique.

2. Endpoint noise—If a pattern is constructed from a data set that is embedded in a larger data set—as is the case in eddy current test analysis—it is sometimes difficult to establish precise limits on points belonging to the pattern and points that do not. Consequently on either end of the pattern curve, points of rapid curvature change that do not contribute to overall appearance may be included. These points are removed by imposing "smoothness" constraints on the ends of the curve. Lines are best fit to the curvature function at both ends, each line being no longer than 2.5% of the total arclength. The lines are interlaced so that one line begins at the midpoint of the preceding line. When three consecutive lines have the same sign slope and small variance, then it is assumed that the endpoints of the curve manifest sufficient smoothness. Any set of data points preceding those manifesting this smoothness are removed. This noise removal technique is a novel feature of DODGER.

3. Small loop noise—Small loops that are unimportant to overall pattern appearance nevertheless display large curvature change at all resolution levels, thereby confounding true pattern recognition. These are removed by first running the recognition analysis at fine resolution (fine resolution values are automatically determined by the pattern subsystem according to data size). All regions of the pattern that display large curvature change over small arclength distance are tested for curve self-crossing. If self-crossing does occur, the points forming the loop are removed and neighboring points are adjusted to smoothly join together. The recognition procedures are then rerun with the modified data set. The realization that small loops pose a problem for true pattern recognition and that they should be treated as noise and removed for purposes of analysis is a novel feature of this program.

The recognition of pattern class allows DODGER to decide what part of a curve is relevant for establishing geometric facts that help to identify the physical anomaly, or anomalies, represented by the pattern. DODGER then invokes the appropriate pattern analysis to supply the required geometric information. For eddy current test analysis, two types of pattern class are of special interest.

FIG.-8 [+ −)/(− +)] and FIG.-C [(+ +)/(− −)]Patterns

The most important input information is the location of the two curvature change edges, i.e., those portions of the figures corresponding to lobe rounding. This information allows a rough estimate of five regions of the curve, the two regions on each end prior to lobe rounding, the two lobe rounding regions, and the intermediate, or transition, region, connecting the rounded lobes.

Significant geometric characteristics are quantified and established as facts to guide DODGER's deduction process. The rules contingent upon the existence of various kinds of pattern related facts can then be activated.

FIG.-V [(+)/(−)] Patterns

FIG.-V patterns are often badly distorted so that they are (+) class patterns only at coarse resolution. The FIG.-V vertex is taken to be that edge that remains at coarse resolution or that edge at fine resolution that is situated closest to the middle of the arclength of the figure. The most important input information is the fine resolution edge locations. A phase vector is computed, defined as that vector that connects the vertex of the FIG.-V to the midpoint of the line connecting the ends of the FIG.-V legs. Computation of the width of the figure at points along the length of the phase vector is also performed. In addition, another vector is drawn from the vertex to the midpoint of the line joining the first and last data points of the curve; this vector is sometimes used to determine pattern phase. Thus, the output information for this figure is (a) two types of phase vectors (magnitude and orientation), and (b) figure width.

Operation of the DODGER System

To start a session with DODGER, the operator selects a collection of tube data files to examine. Then from that set the operator chooses specific tubes, one at a time, to analyze. These selections, along with any special system configuration options the operator chooses to select, are made in DODGER's menu system. Once a tube has been selected, its data are analyzed in the graphic display using two different modes.

Figure 9:
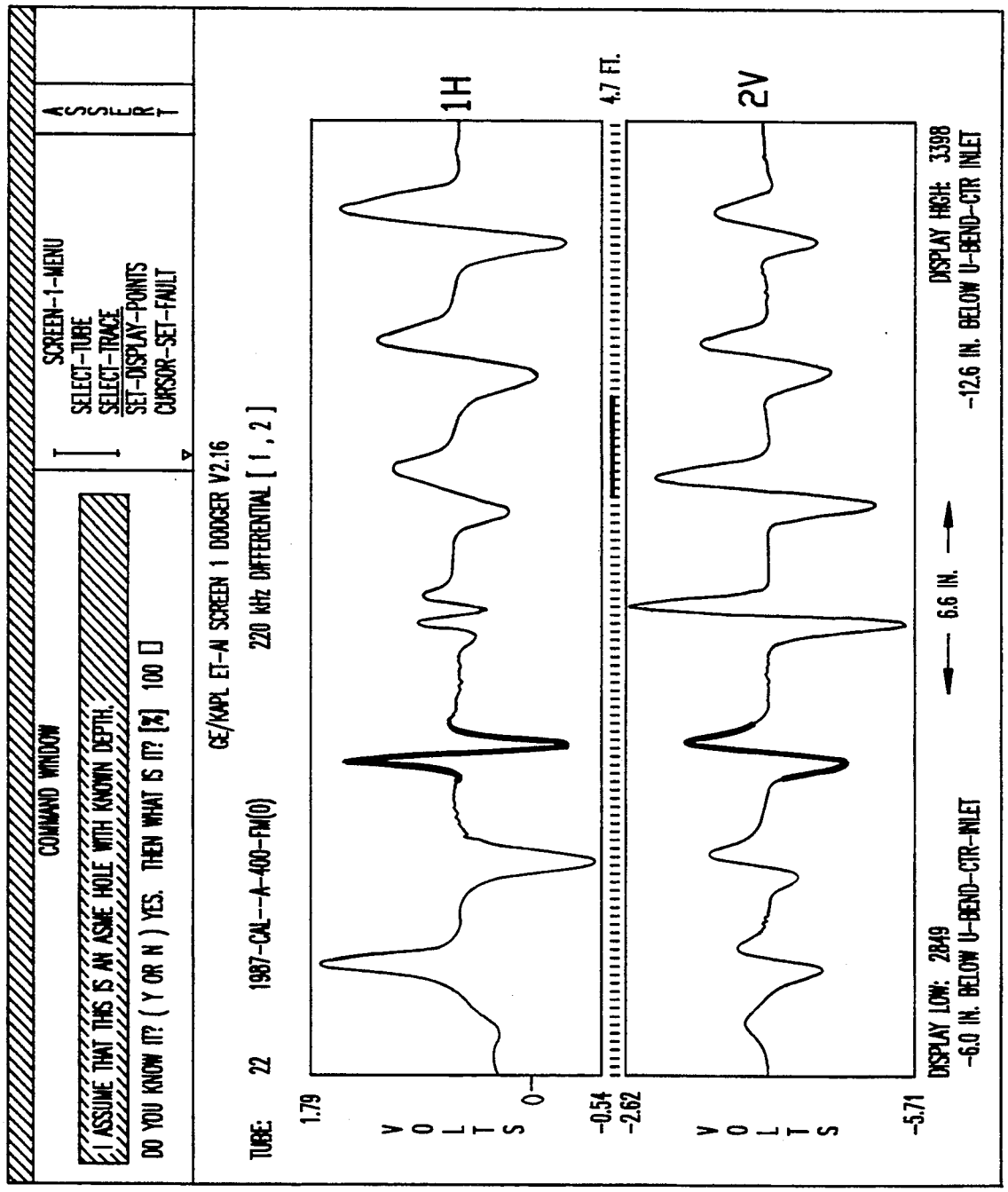
FIG. 9 shows the DODGER system identifying an ASME flaw on a calibration tube.

The first mode displays two strip charts that show the data in a time plot mode where either the vertical or horizontal component of the signal is displayed versus time as shown in FIG. 9. Use of the time plot mode allows the operator to review data from the entire length of a tube and highlight features to be analyzed. The axial position of the probe is derived from the signal responses obtained from structural supports in the heat exchanger which are known locations. DODGER marks the position of the supports and automatically calculates the position of an indication with respect to these supports.

Figure 10:
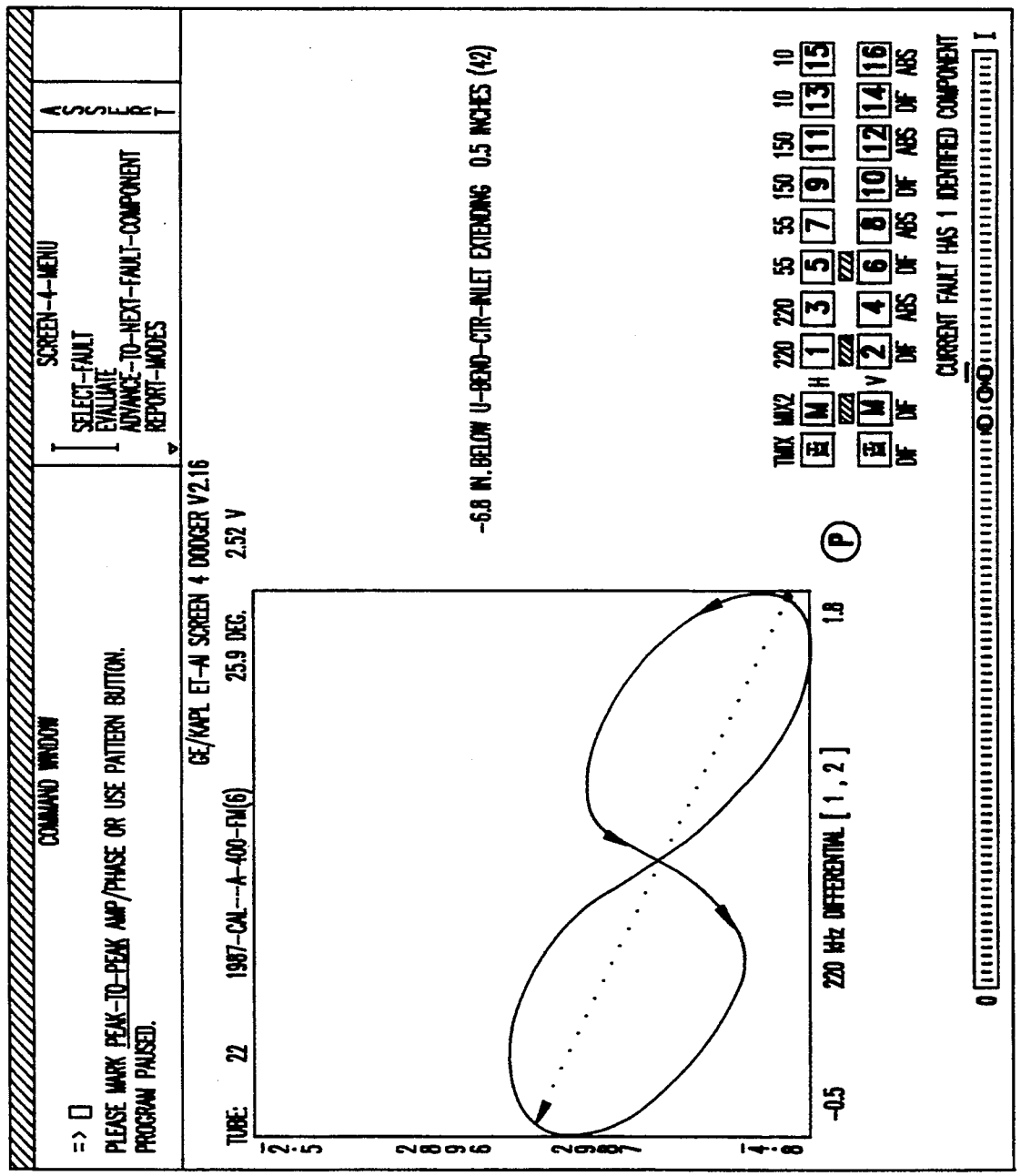
FIG. 10 shows DODGER's normalization process as it is seen by a user.

The second mode allows the operator to view signals in the Lissajous mode where the vertical and horizontal components of the signal are plotted against each other as shown in FIG. 10. This mode is used for analysis of a potential flaw. Four windows are also provided in the Lissajous mode to display data in the time plot mode if desired by an operator.

Figure 11:
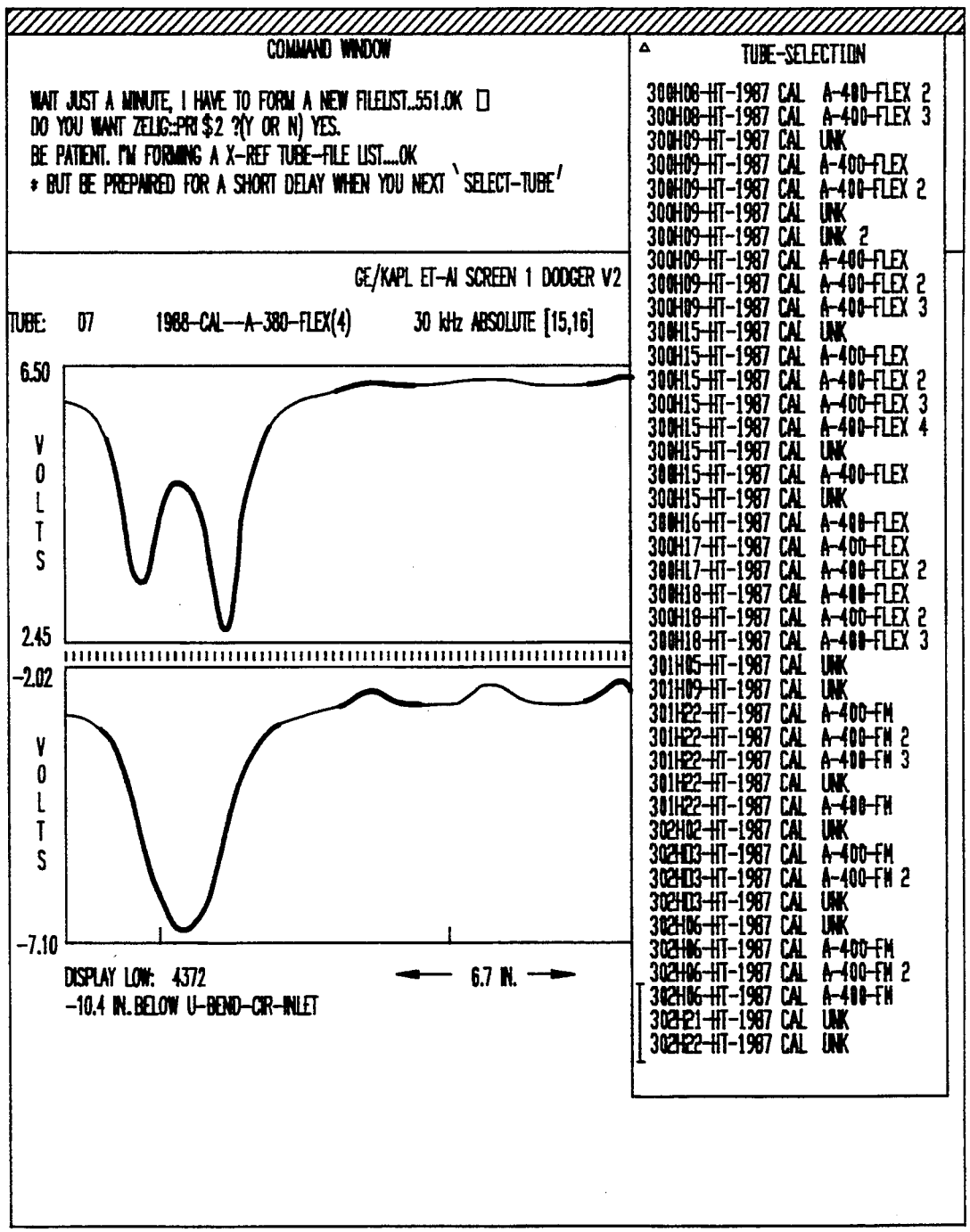
FIG. 11 shows the use of a select-tube menu of the DODGER expert system.

A method of calibrating the DODGER system will now be discussed. Most calibration functions are performed automatically by DODGER. FIG. 9 illustrates the graphical display DODGER presents for the purpose of locating these features. The operator begins by selecting a calibration standard from the select-tube menu as shown in FIG. 11. DODGER displays all of the calibration standards at the bottom of the select-tube menu. In this manner, all of the applicable calibration runs are immediately accessible to the operator.

Once the operator has selected a calibration standard for display, data from that run are displayed in the time plot mode format. Any two channels' "signals" may be selected for display on the strip charts at the operator's discretion. DODGER attempts to display the most meaningful part of the data file. DODGER provides ZOOM and PAN functions which enable the operator to quickly locate the features of interest on the calibration standard. Once the features have been located, DODGER asks the operator to identify them. DODGER is aware of three different classes of features on the calibration tube: ASME flaws, support rings and roll transition (profilometry) standards. FIG. 9 illustrates the identification of an ASME flaw. Once these features are identified, the operator then switches to the Lissajous mode.

Figure 12:
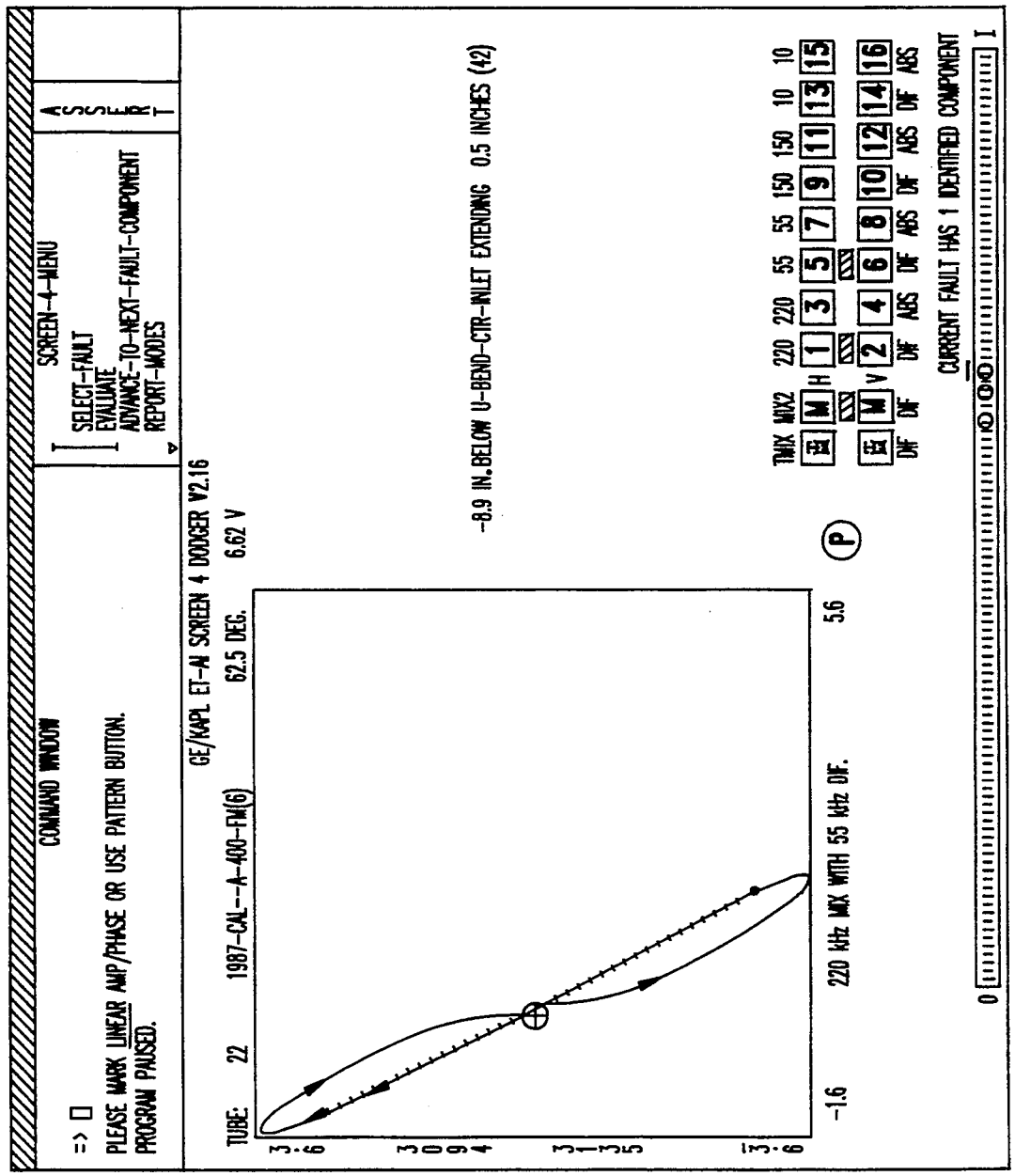
FIG. 12 shows DODGER calibrating a mix output as shown on the computer screen to a user.

Once the Lissajous mode has been selected, DODGER proceeds with the calibration process. From this point, DODGER can automatically complete the calibration process (normalization, rotation, two and three frequency mix setups and depth calibration). FIGS. 10 and 12 illustrate the normalization and mix calibration portion of this process.

Figure 13:
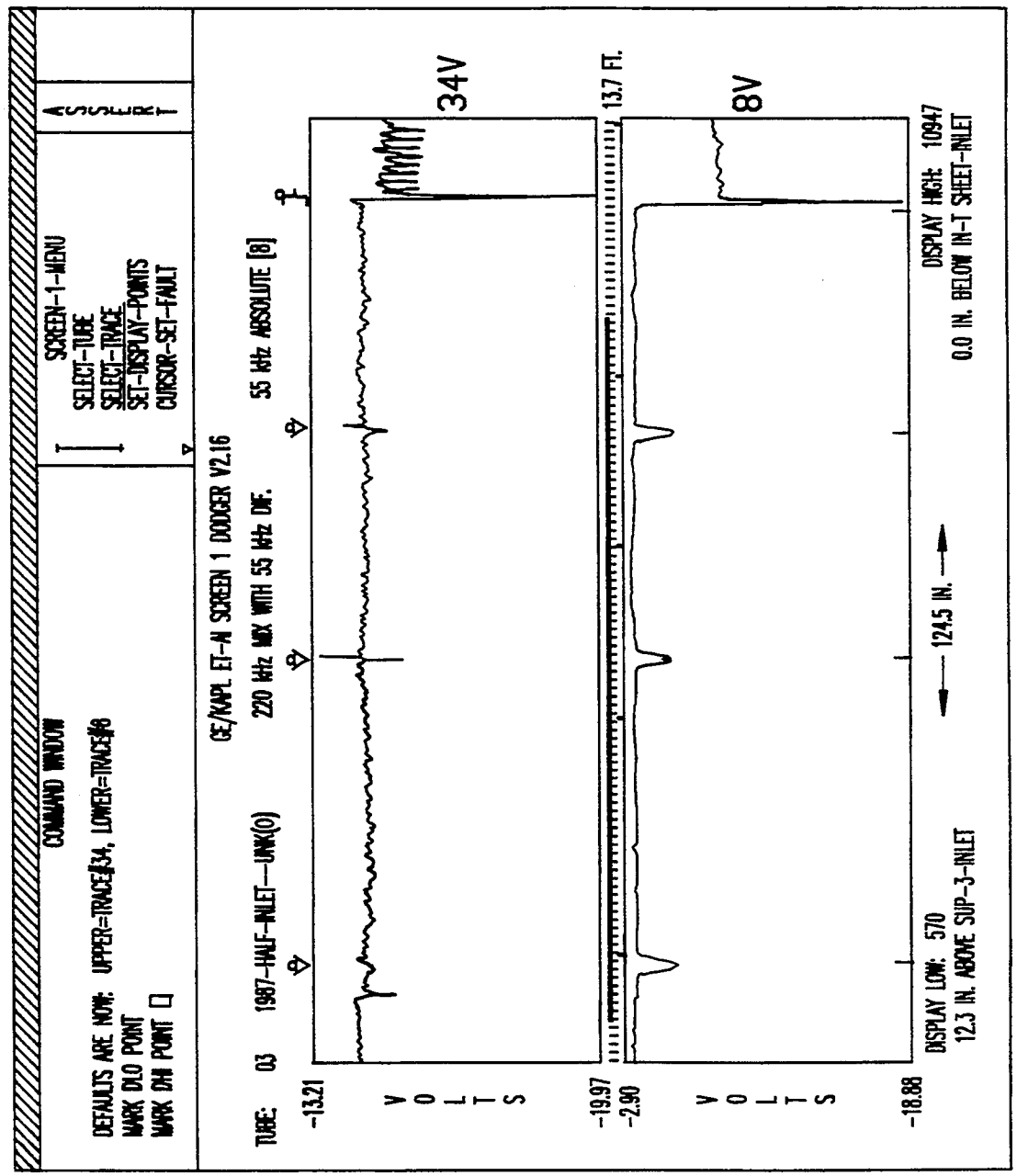
FIG. 13 defect screening by an operator on the DODGER system.

Now the flaw identification and analysis section of DODGER will be illustrated. Once the calibration process is complete, the operator may select any available tube from ET data 70 for analysis. The current calibration is permanently associated with the data tube for future reference. The eddy current data for the selected tube is displayed in the time plot format. FIG. 13 illustrates the normal signals displayed (vertical components of the mix channel and vertical component of the lower frequency absolute channel). As before, these traces may be changed at the operator's discretion. Flaws are identified by the operator.

Figure 14:
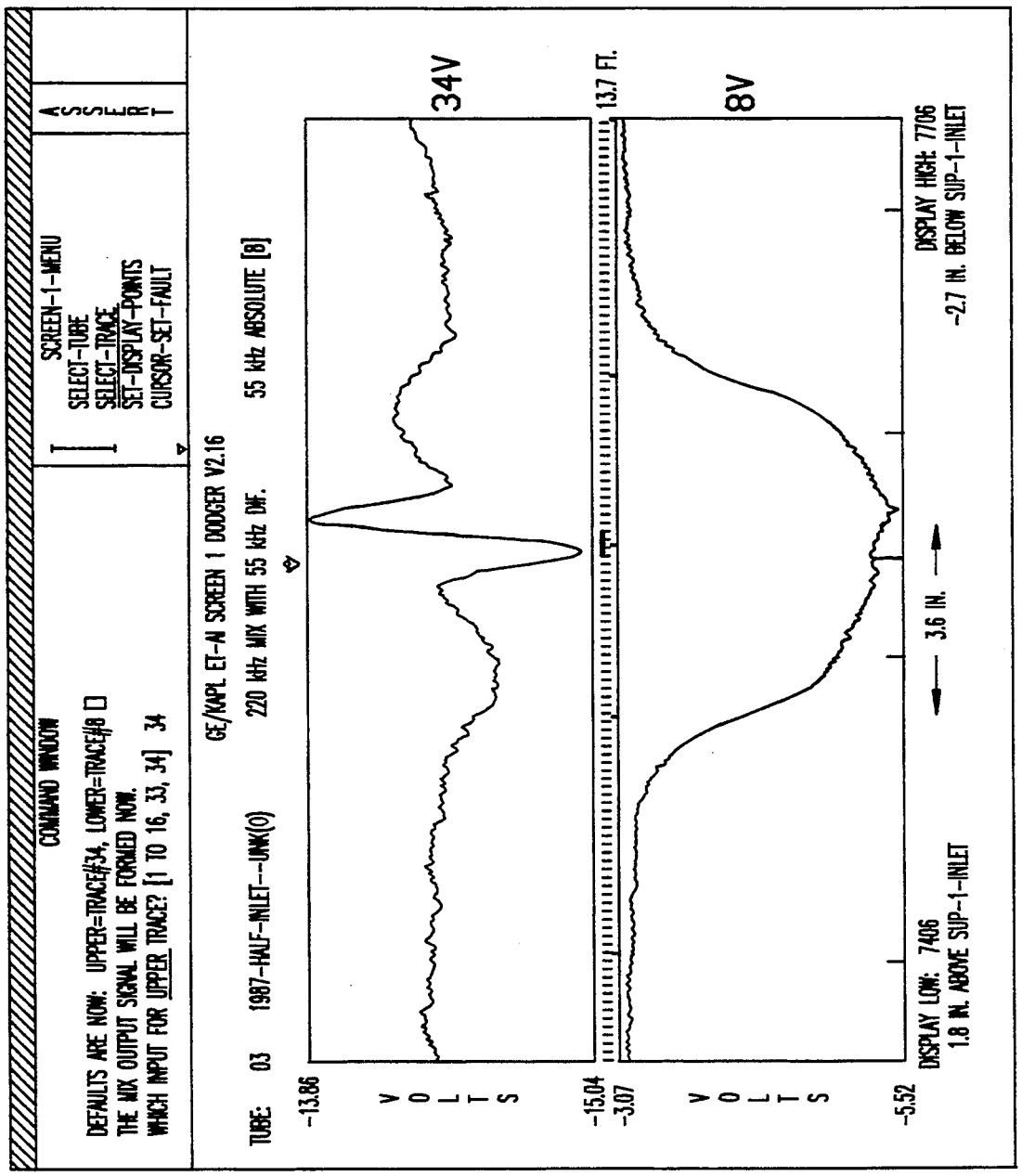
FIG. 14 shows identification of a possible defect by an operator on the DODGER system.

FIG. 14 shows the process of flaw identification. In this case, an indication has been detected on the mixed channel, and the operator has selected that area for further evaluation. At the operator's discretion, DODGER responds with the Lissajous patterns of four different channels for review. The operator can then choose whether or not the indication should be evaluated. If the operator chooses to evaluate the indication, DODGER highlights the area. The Lissajous mode is then used to analyze this indication.

Figure 3:
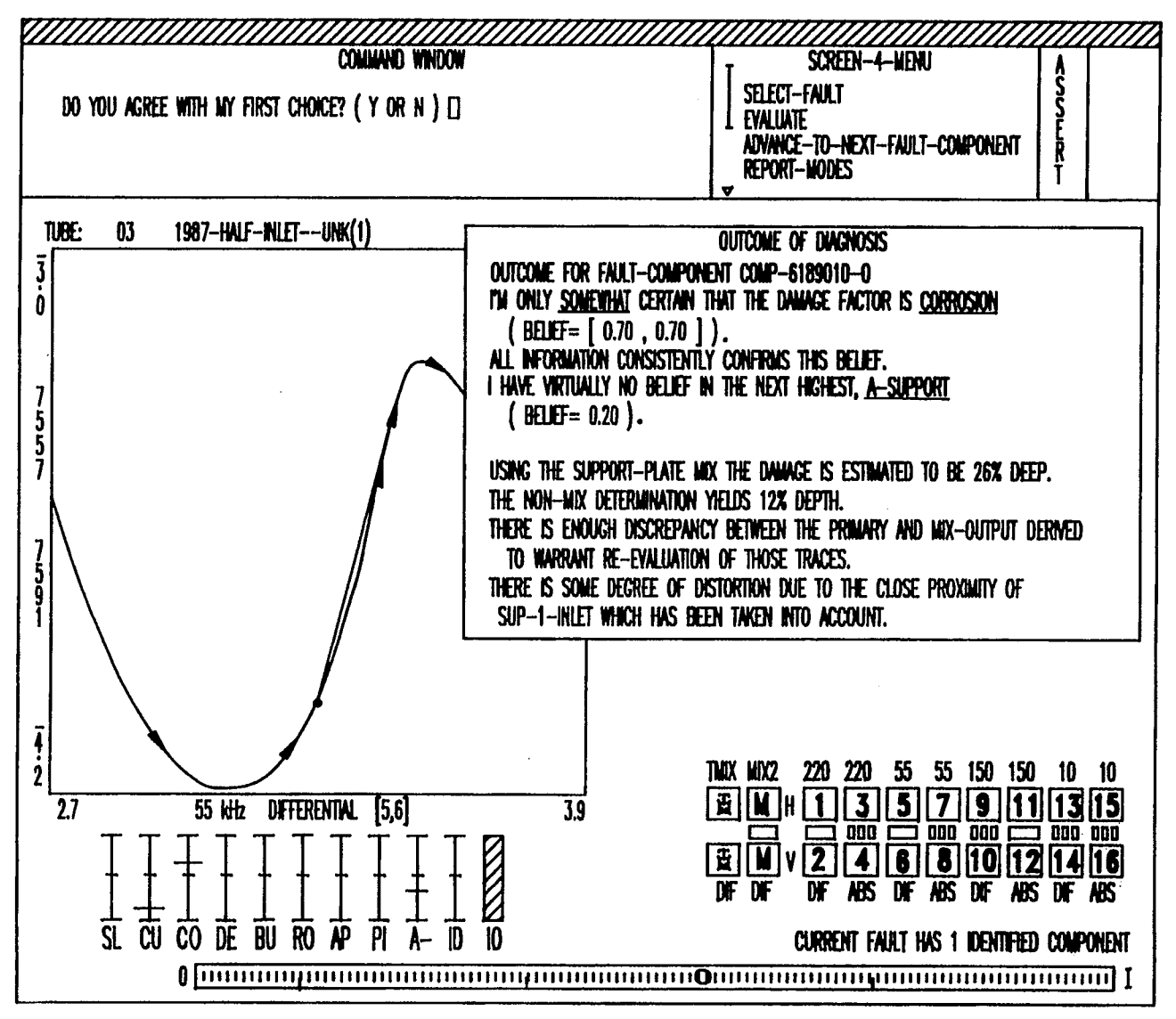
Figure 15:
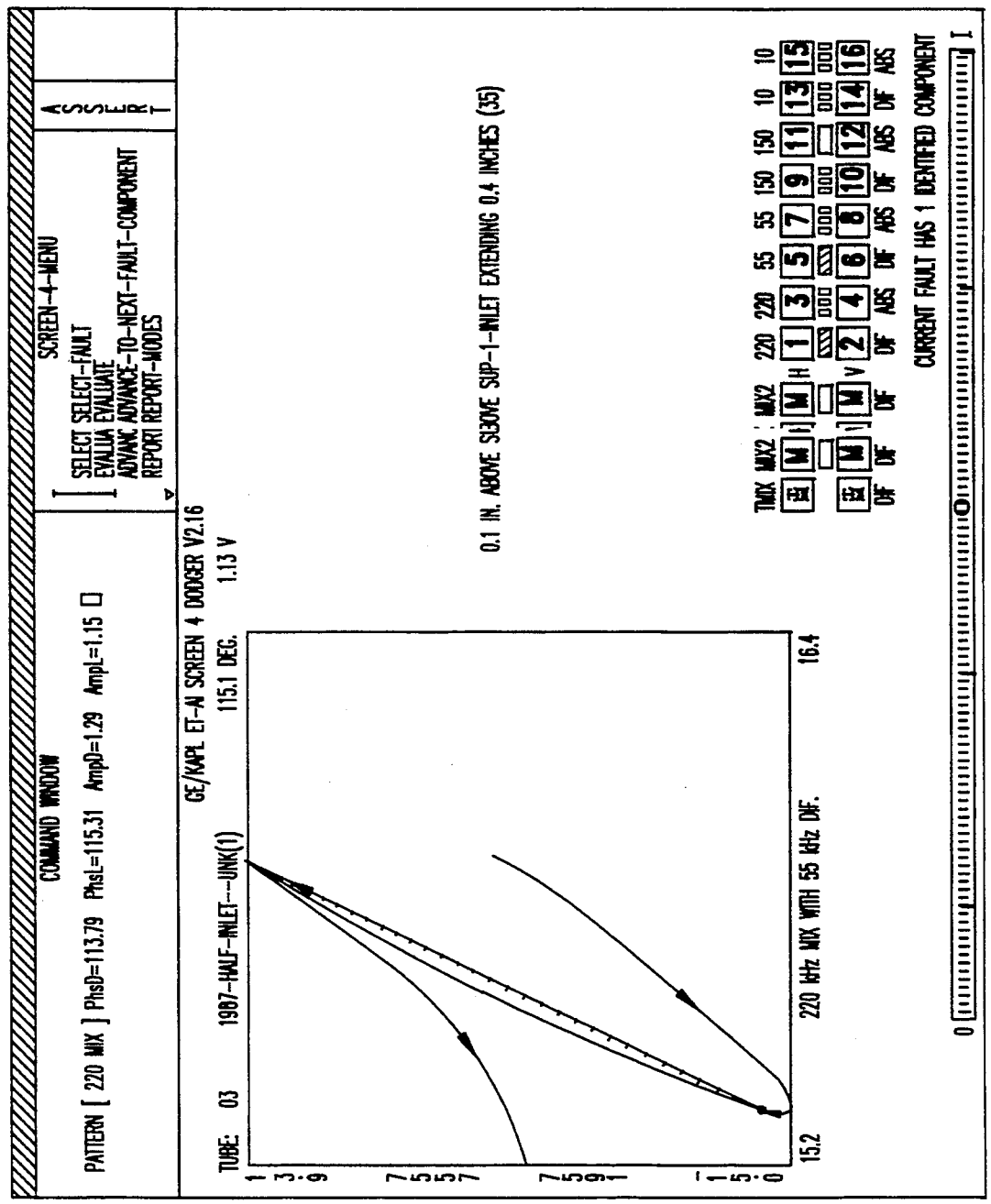
FIG. 15 shows evaluation of the mix output by an operator on the DODGER system.
Figure 16:
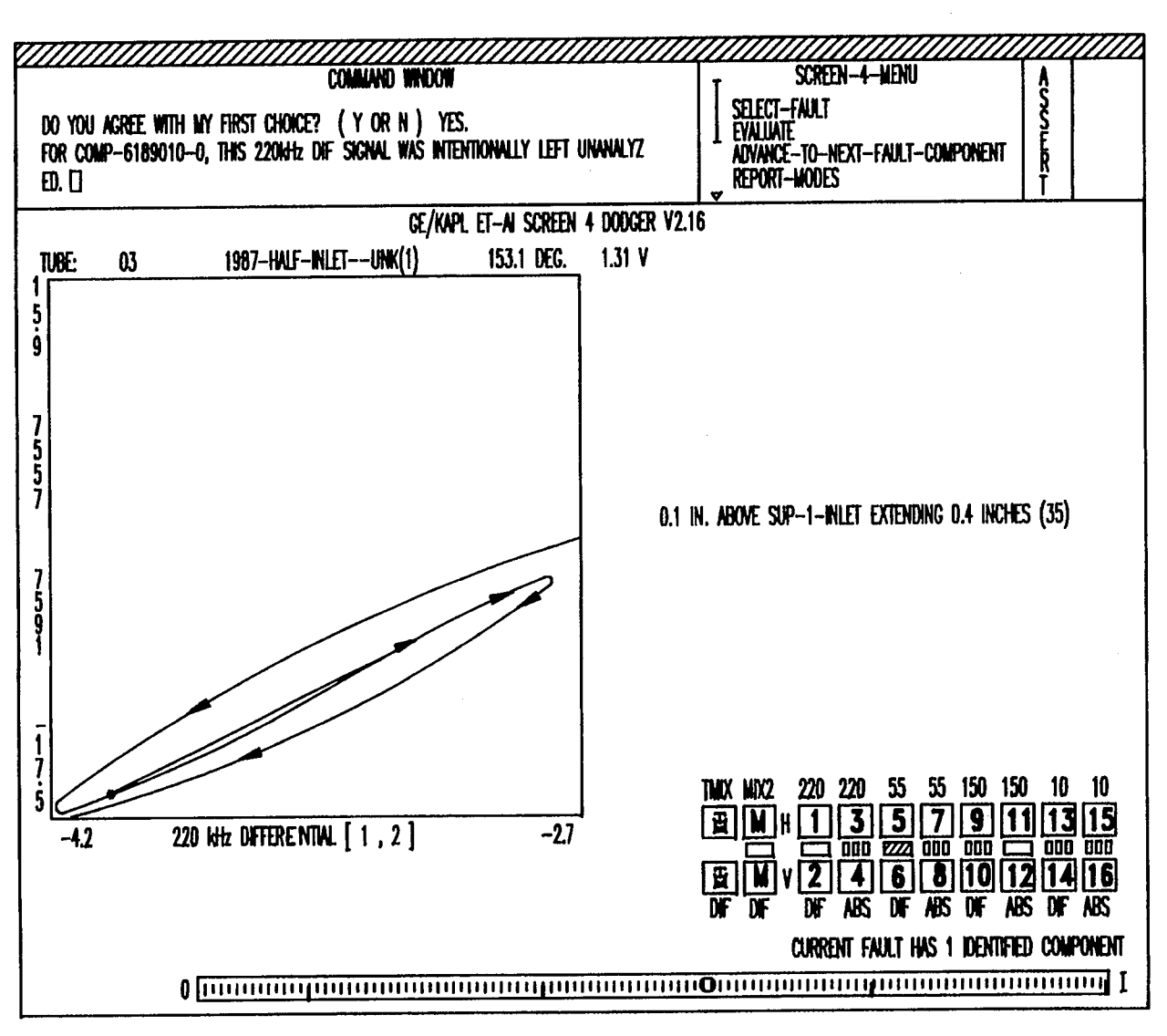
Figure 17:
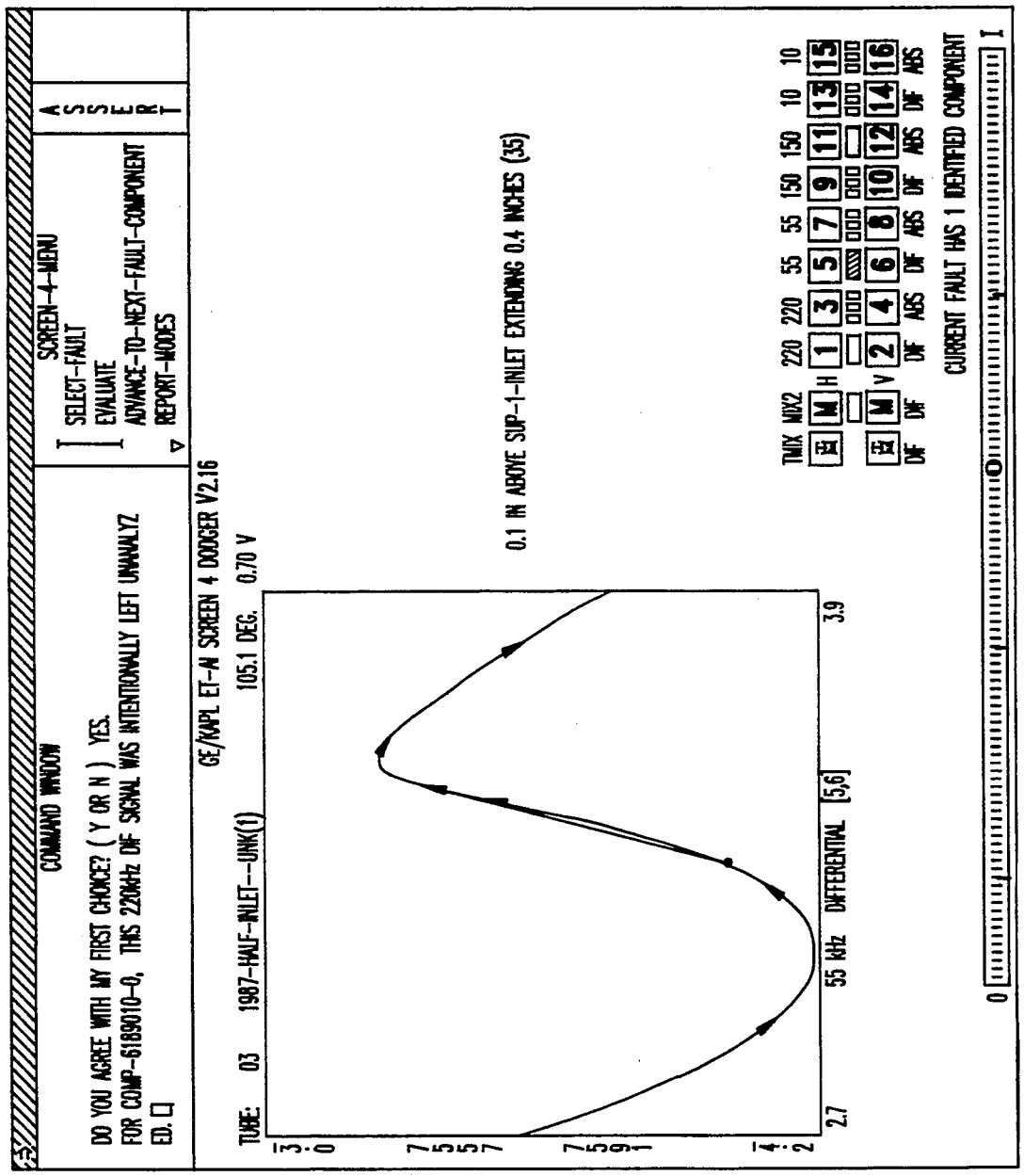
FIG. 17 shows evaluation of lower frequency data by the DODGER system.

In the Lissajous mode, various frequencies are examined by DODGER until a diagnosis can be reached. The operator may elect to run DODGER in automatic mode—whereby all indications are classified and measured by pattern recognition without operator input—or semi-automatic or manual modes. In semi-automatic mode, the operator is asked to confirm or override DODGER's pattern recognition results. In manual mode, DODGER does not perform its pattern recognition and the operator must measure the displayed indications. FIGS. 15–17 illustrate the process used to make these measurements in semi-automatic mode. Note that in FIG. 15, the operator has corrected the measurement made by the pattern recognition (solid line overrides DODGER's proposed dashed line). FIG. 3 shows the diagnosis reached by DODGER in this case.

Figure 4:
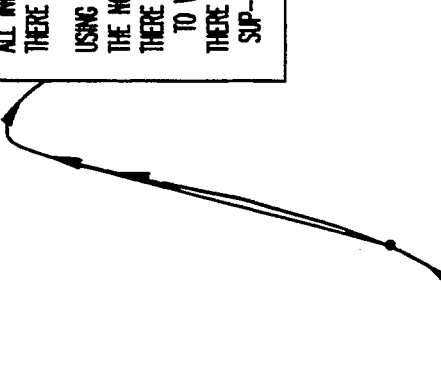
FIG. 4 shows DODGER's response to an operator's assertion shown in FIG. 18.
Figure 18:
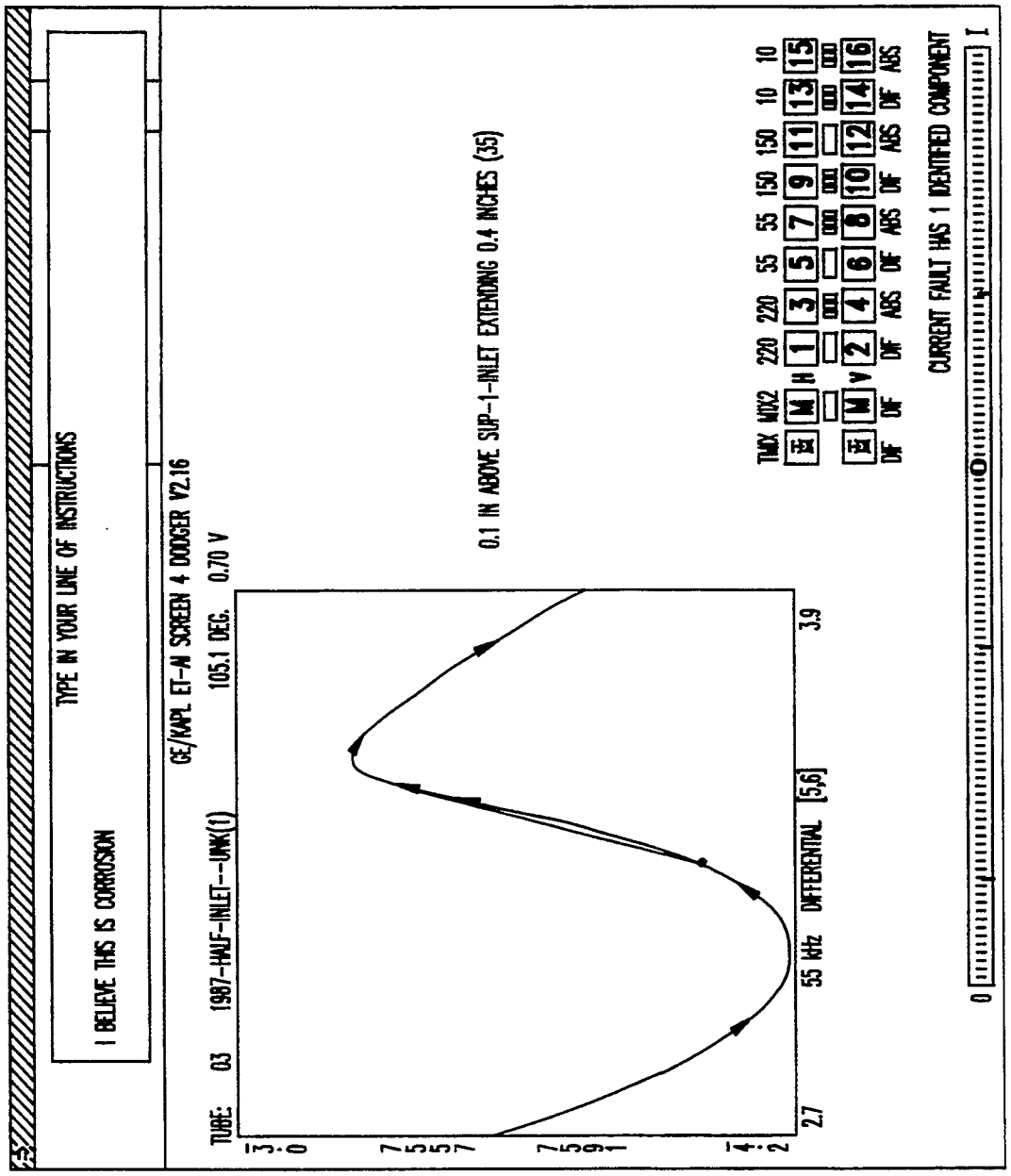
FIG. 18 shows how an operator asserts his opinion to the DODGER system.

DODGER also allows the operator to assert his own opinion if he disagrees with the diagnosis. FIG. 18 illustrates this process. Commands are entered in simple English, and are evaluated by DODGER. If further analysis is suggested by the operator's assertion, DODGER will proceed and display a new diagnosis as shown in FIG. 4.

FIGS. 3, 4, 13–17 and 18 show the results of an analysis performed on an indication in a heat exchanger tube. In this case, DODGER successfully diagnosed the condition and provided sizing of the flaw. No operator input was required once the indication had been located. Note that in the case of FIG. 3, some degree of conflict exists between the two of the traces (prime and mixed). The discrepancy in the size estimates was sufficient to lower the belief in corrosion as a damage mechanism. This case is an example of DODGER's ability to reason with uncertainty and provide a quantitative measure of the reliability of a diagnosis.

Although the preferred embodiment of the present invention is its use to analyze eddy current data from heat exchanger tubes, the system can be broadly applied to any eddy current inspection work, e.g., condenser tubes, pipes, tube joints, etc. Furthermore, it could be extended to operate with various types of eddy current probes such as pancake coil or axial wound coil designs.

What is claimed is:

1. A computer-based method of analyzing eddy current signals to provide information about flaws in a metallic object, using an expert system, wherein said eddy current signals are obtained prior to using said expert system by passing an eddy current probe along said metallic object, detecting any change in current by a change in electrical impedance, and recording said change in electrical impedance as electrical signal data on a storage device, comprising the steps of:
   a) retrieving said electrical signal data for one said metallic object from said storage device for analysis;
   b) calibrating said expert system;
   c) associating calibration information with said data;
   d) displaying said data as graphical data patterns;
   e) analyzing said graphical data patterns in a consistent and uniform manner, wherein said analyzing includes applying a rule base and a knowledge base, said knowledge base including reasoning with uncertainty and pattern recognition to interpret said electrical signal data; and wherein said pattern recognition comprises obtaining geometric parameters from said graphical data patterns and storing said parameters in said knowledge base; and
   f) presenting a diagnosis of said flaws.

2. The method of claim 1, wherein said analysis step includes analysis of hypotheses suggested by an operator.

3. The method of claim 1, wherein said calibration step includes signal mixing calibration, depth calibration, signal rotation and normalization.

4. The method of claim 1, wherein said analysis step includes using fuzzy set representation to analyze said geometric parameters stored in said knowledge base obtained from said graphical data patterns.

5. The method of claim 1, wherein said analysis step includes recognizing conflicts in said electrical signal data.

6. The method of claim 1, wherein said analysis step includes distinguishing between lack of knowledge and conflicting evidence.

7. The method of claim 1, wherein said analysis step includes weighting a set of rules in order to control contribution of those rules to said diagnosis.

8. The method of claim 1, wherein said pattern recognization step includes classifying said patterns according to curvature functions.

9. The method of claim 1, wherein said pattern recognition step includes removing noise from said patterns including endpoint noise and small loop noise.

10. The method of claim 1, wherein said geometric parameters obtained in said pattern recognition step include but are not limited to phase vectors, amplitude and width of lobes.

11. The method of claim 1 wherein said metallic object is a heat exchanger tube.

12. The method of claim 1 wherein said analysis step includes operator interaction with said expert system.

13. The method of claim 1 wherein said calibration step includes selecting a calibration standard and identifying features of interest on said standard.

14. The method of claim 1 wherein said analysis step further comprises generating a belief value for said diagnosis.

15. The method of claim 14 wherein said generating step uses an optimally chosen minimal amount of data to achieve a belief in a most likely diagnosis.

16. The method of claim 15 wherein said generating step further comprises automatically and dynamically selecting a next frequency signal for analysis in order to minimize said data used in said most likely diagnosis.

17. The method of claim 14 wherein said generating step further comprises automatically and dynamically determining when a sufficient amount of said data has been analyzed to generate an optimal belief value in said diagnosis.

18. The method of claim 17 wherein said determining step further comprises:
   1) pursuing a most believable and plausible hypothesis based on said data; and
   2) pursuing said hypothesis whose belief value increases most as a new frequency signal is analyzed.

* * * * *